United States Patent
Yang et al.

(10) Patent No.: US 12,303,897 B2
(45) Date of Patent: May 20, 2025

(54) MICRO- AND NANO-FLUIDIC CHIP, METHOD OF FABRICATING THE SAME, AND APPLICATIONS THEREOF

(71) Applicant: SHENZHEN INSTITUTES OF ADVANCED TECHNOLOGY, Shenzhen (CN)

(72) Inventors: Hui Yang, Shenzhen (CN); Rui Hao, Shenzhen (CN); Yi Zhang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 710 days.

(21) Appl. No.: 17/565,485

(22) Filed: Dec. 30, 2021

(65) Prior Publication Data
US 2022/0184620 A1   Jun. 16, 2022

Related U.S. Application Data

(63) Continuation of application No. PCT/CN2019/125436, filed on Dec. 14, 2019.

(51) Int. Cl.
*B01L 3/00* (2006.01)
*A61K 45/06* (2006.01)
(Continued)

(52) U.S. Cl.
CPC ........ *B01L 3/502753* (2013.01); *A61K 45/06* (2013.01); *B01L 3/502707* (2013.01);
(Continued)

(58) Field of Classification Search
CPC ......... B01L 3/502746; B01L 3/502707; B01L 3/502753; B01L 3/502761;
(Continued)

(56) References Cited

U.S. PATENT DOCUMENTS

| | | | | |
|---|---|---|---|---|
| 2008/0180188 | A1* | 7/2008 | Beerling | B82Y 15/00 333/26 |
| 2008/0280785 | A1* | 11/2008 | Tseng | B01L 3/0255 506/40 |

(Continued)

FOREIGN PATENT DOCUMENTS

| | | |
|---|---|---|
| CN | 101561446 A | 10/2009 |
| CN | 102059161 A | 5/2011 |

(Continued)

OTHER PUBLICATIONS

International Search Report issued in corresponding International application No. PCT/CN2019/125436, mailed Aug. 13, 2020.

*Primary Examiner* — Shogo Sasaki

(57) ABSTRACT

Provided is a micro- and nano-fluidic chip, including at least one nanochannel array layer and at least one microchannel array layer that are alternately stacked. The at least one nanochannel array layer includes nanochannels, the at least one microchannel array layer includes input units and/or output units. The input unit includes inlet microchannel arrays and inlets, and the output unit includes outlet microchannel arrays and outlets. The inlet microchannel array includes inlet microchannels, the outlet microchannel array includes outlet microchannels, and the inlet microchannels and the outlet microchannels are connected through the nanochannels.

6 Claims, 12 Drawing Sheets

PDMS    Microchannel    Glass substrate    Nanochannel

(51) Int. Cl.
  *G03F 7/038* (2006.01)
  *G03F 7/039* (2006.01)
  *G03F 7/20* (2006.01)
  *G03F 7/32* (2006.01)
  *G03F 7/38* (2006.01)
  *G03F 7/40* (2006.01)
  *B82Y 40/00* (2011.01)

(52) U.S. Cl.
  CPC .......... *G03F 7/0382* (2013.01); *G03F 7/0392* (2013.01); *G03F 7/20* (2013.01); *G03F 7/32* (2013.01); *G03F 7/38* (2013.01); *G03F 7/40* (2013.01); *B01L 2200/12* (2013.01); *B01L 2300/0819* (2013.01); *B01L 2300/0896* (2013.01); *B82Y 40/00* (2013.01)

(58) Field of Classification Search
  CPC ..... B01L 2300/0896; B01L 2300/0874; B01L 2200/0647; B01L 2400/08; B01L 2300/0887; B01L 2200/12; B01L 2300/0819; B01L 2300/0867; G03F 7/40; G03F 7/32; G03F 7/38; G03F 7/20; G03F 7/0382; G03F 7/0392; A61K 45/06; A61K 9/0097; B82Y 40/00
  See application file for complete search history.

(56) References Cited

U.S. PATENT DOCUMENTS

| | | | |
|---|---|---|---|
| 2009/0214392 A1* | 8/2009 | Kameoka | B01L 3/502761 156/60 |
| 2011/0027873 A1* | 2/2011 | Cho | B81C 1/00103 422/69 |
| 2018/0200715 A1 | 7/2018 | Solis et al. | |
| 2021/0229977 A1* | 7/2021 | Ma | B01L 3/502715 |
| 2022/0342304 A1* | 10/2022 | Yao | G03F 7/095 |
| 2024/0261785 A1* | 8/2024 | Li | B01L 3/502761 |

FOREIGN PATENT DOCUMENTS

| | | |
|---|---|---|
| CN | 110560185 A | 12/2019 |
| CN | 110560186 A | 12/2019 |
| WO | 2015112323 A1 | 7/2015 |

\* cited by examiner

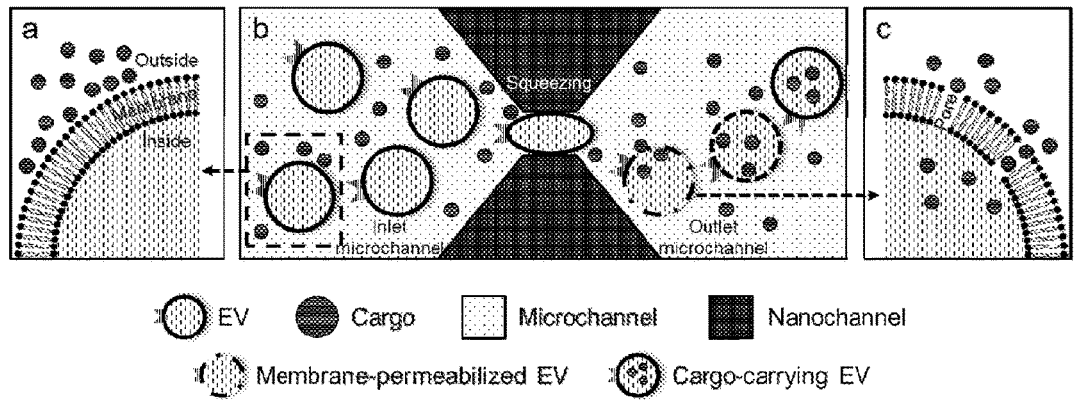

Fig. 15

| Injecting a solution of biological particles into the inlet of the micro- and nano-fluidic chip, where the biological particles comprise at least one of extracellular vesicles, nanovesicles, membrane vesicles secreted by microorganisms, subcellular particles with a size of 30 nm to 2000 nm and having a membrane structure, cell membrane nanoparticles with a size of 30 nm to 2000 nm , artificially synthesized nanoparticles with a size of 30 nm to 2000 nm wrapped in phospholipid bilayer, liposomes with a diameter of 30 nm to 2000 nm, or viral vectors | ←S400 |

| Allowing the solution of the biological particle to enter the nanochannels through the inlet microchannel array, where a depth of the nanochannel is less than or equal to a diameter of the biological particle so that a membrane of the biological particle is mechanically squeezed in the nanochannel thus introducing pores in the membrane | ←S500 |

| Collecting the biological particle solution treated by the chip from the outlet, and mixing the cargos with the squeezed biological particle solution, so that the cargo molecules diffuse into the interior of the biological particles from the outside through the pores, and further obtaining a cargo-carrying biological particle by purification process | ←S600 |

Fig. 16

MICRO- AND NANO-FLUIDIC CHIP, METHOD OF FABRICATING THE SAME, AND APPLICATIONS THEREOF

CROSS-REFERENCE TO RELATED APPLICATIONS

This application is a continuation of co-pending International Patent Application Number PCT/CN2019/125436, filed on, the disclosure of which is incorporated herein by reference in its entirety.

TECHNICAL FIELD

This disclosure relates to the field of microelectromechanical system technology, microfluidic technology and nanofluidic technology, and more particularly relates to a micro- and nano-fluidic chip, a method of fabricating the same, and applications thereof.

BACKGROUND

With the rise of nanotechnology, a variety of nano-delivery systems (NDSs) have been proposed in succession, aiming to carry small molecules, nucleic acids, proteins, or other exogenous cargos into the body or focal lesion, which is not only helpful for the diagnosis and treatment of cancers, infectious diseases, cardiovascular diseases, and neurodegenerative diseases, etc., but are also conducive to improving the therapeutic effect and reducing negative effects such as organ toxicity. Thus, the construction of new types of NDSs has major theoretical significance and practical value for experimental research and clinical application.

For the time being, commonly used NDSs include nanoparticles, liposomes, and viral vectors, etc. These NDSs, however, face a variety of problems in clinical applications, such as organ toxicity, immune clearance, insertional mutagenesis, and short circulation duration within the body. Biological particles such as extracellular vesicles (EVs) having a diameter of about 30 nm~2000 nm, which originate from the secretion of cells, the secretion of microorganisms, or may be derive from artificial synthesis, are regarded as a natural communication medium or delivery vehicle. They can not only realize the transfer and transportation of substances, but also have the advantages of low immunogenicity, biodegradability, non-toxicity, high carrying capacity, and strong tissue penetration. Therefore, they have been regarded as a new type of NDS in recent years.

In order to deliver exogenous cargos into the interior of biological particles such as EVs, commonly used methods include incubation and electroporation. The incubation method includes mixing the cargos with the biological particles uniformly under a certain temperature, and so the cargo molecules gradually diffuse into the interior of the biological particles along the concentration gradient thereby achieving cargo loading. Although the incubation method is simple and easy to operate, this method generally has a problem of low cargo-loading efficiency. Electroporation, as another commonly used cargo-loading method, includes stimulating the biological particles by applying an electric field so that some temporary pores would appear on the membrane surface. As such, the cargo molecules are convectively transported into the biological particles through the pores. Then after a certain period of time, the membrane of biological particles returns to their original intact state. In this way, the cargos are packaged in the biological particles, thus accomplishing the cargo-loading process. While this method improves the cargo-loading efficiency, the external electric field may induce excessive damages on both biological particles such as EVs and their carrying cargos.

Micro-/Nano-fluidics is a technology for studying and applying the properties of fluids and their contents at the micro- or nano-scale. Microfluidic chips have been used in cellular loading, but there are no micro- and nano-fluidic chips applied to the study of cargo loading of biological particles such as EVs.

SUMMARY

In view of this, there is a need to provide a micro- and nano-fluidic chip that can be used for cargo loading of biological particles such as EVs, a method of fabricating the micro- and nano-fluidic chip, and a method of preparing cargo-carrying biological particles.

There is provided a micro- and nano-fluidic chip, comprising at least one nanochannel array layer and at least one microchannel array layer, where the at least one nanochannel array layer and the at least one microchannel array layer are alternately stacked.

The at least one nanochannel array layer includes at least one nanochannel.

The at least one microchannel array layer includes an input unit and/or an output unit. The input unit includes an inlet microchannel array and at least one inlet, and the output unit includes an outlet microchannel array and at least one outlet. The inlet microchannel array includes at least one inlet microchannel, and the outlet microchannel array includes at least one outlet microchannel, where the at least one inlet microchannel and the at least one outlet microchannel are alternately arranged at intervals. The at least one inlet is connected to the at least one inlet microchannel, and the at least one outlet is connected to the at least one outlet microchannel. Each pair of inlet microchannel and outlet microchannel are bridged by the at least one nanochannel.

In the case where the at least one microchannel array layer is one layer, the microchannel array layer includes the input unit and the output unit. When the nanochannel array connects the at least one inlet microchannel array and the at least one outlet microchannel array, the extension direction of the at least one nanochannel is set at an angle of 0°~90° with the microchannel array layer.

In the case where the microchannel array includes two or more layers, one of the microchannel array layers includes the input unit, and another of the microchannel array layers includes the output unit, and the nanochannel array layer is arranged between every two adjacent microchannel array layers. When the nanochannel array connects the inlet microchannel array and the outlet microchannel array, the extension direction of the at least one nanochannel is set at an angle of 0°~ 90° with the microchannel array layers.

In one embodiment, the at least one nanochannel array layer is made of polydimethylsiloxane (PDMS), glass, quartz, silicon wafer, silicon nitride wafer, silicon dioxide wafer, silicon carbide wafer, poly (methyl methacrylate) (PMMA), parylene-C, polycarbonate (PC), cyclic olefin copolymer (COC), cyclic olefin polymer (COP), polypropylene (PP), photocurable resin, or soft thermoplastic elastomer (sTPE), etc., and the at least one microchannel array layer is made of PDMS, glass, quartz, silicon wafer, silicon nitride wafer, silicon dioxide wafer, silicon carbide wafer, PMMA, parylene-C, PC, COC, COP, PP, photocurable resin, or sTPE, etc.

In one embodiment, in the case where the at least one nanochannel array includes at least two nanochannels, the nanochannels of the nanochannel array layer are arranged at an angle of 0° to 90° with respect to one another.

In one embodiment, in the case where there are one inlet microchannel and one outlet microchannel, the inlet microchannel and the outlet microchannel are arranged at an angle of 0° to 90° with respect to each other; or In the case where there are provided two or more inlet microchannels and two or more outlet microchannels, the inlet microchannels are arranged in parallel, the outlet microchannels are arranged in parallel, and the inlet microchannels are arranged in parallel with the outlet microchannels forming a parallel interdigitated layout; or In the case where there are provided two or more inlet microchannels and two or more outlet microchannels, the inlet microchannels are arranged at an angle greater than 0° and less than or equal to 90° with respect to each other, the outlet microchannels are arranged at an angle greater than 0° and less than or equal to 900 with respect to each other, and the inlet microchannels and the outlet microchannels are arranged to form an oblique interdigitated layout; or the at least one inlet microchannel has a circular shape, the at least one outlet microchannel has an annular shape, and the at least one inlet microchannel and the at least one outlet microchannel form a circular interdigitated layout; or the at least one inlet microchannel has an annular shape, the at least one outlet microchannel has a circular shape, and the at least one inlet microchannel and the at least one outlet microchannel form a circular interdigitated layout; or the at least one inlet microchannel has a spiral shape, the at least one outlet microchannel has a spiral shape, and the at least one inlet microchannel and the at least one outlet microchannel form a spiral interdigitated layout.

In one embodiment, the at least one inlet microchannel has a depth of 1 μm to 1000 μm, and the at least one outlet microchannel has a depth of 1 μm to 1000 μm;

in the case where the at least one nanochannel has a rectangular parallelepiped shape, the at least one nanochannel has a depth dimension of 10 nm to 5000 nm, and a width dimension of 10 nm to 1000 μm; or in the case where the at least one nanochannel has a cylindrical shape, the at least one nanochannel has a diameter of 10 nm to 5000 nm.

There is also provided a method of fabricating a micro- and nano-fluidic chip, including:

fabricating a plurality of nanochannels in the first substrate to obtain a nanochannel array layer;

creating an input unit and/or an output unit in the second substrate, where the input unit includes an inlet microchannel array and at least one inlet, and the output unit includes an outlet microchannel array and at least one outlet, thereby obtaining a microchannel array layer; the inlet microchannel array includes at least one inlet microchannel, and the outlet microchannel array includes at least one outlet microchannel; the at least one inlet microchannel and the at least one outlet microchannel are alternately arranged at intervals; and the inlet is connected to the at least one inlet microchannel, and the outlet is connected to the at least one outlet microchannel.

alternately stacking and bonding the at least one nanochannel array layer and at least one microchannel array layer to obtain the micro- and nano-fluidic chip, wherein the at least one inlet microchannel and the at least one outlet microchannel are connected through the plurality of nanochannels.

In one embodiment, the plurality of nanochannels are fabricated in the first substrate by etching, nanoimprinting, hot embossing lithography, soft photolithography based on PDMS replica molding, injection moulding, 3D printing, or laser micromachining, etc.

In one embodiment, the operation process of fabricating the plurality of nanochannels in the first substrate to obtain the nanochannel array layer is as follows.

A positive photoresist layer is coated on the surface of the first substrate. After soft baking, an exposure treatment is performed using a nanochannel mask. Then the exposed first substrate is immersed in a developer solution for development. After hard baking of the patterned photoresist film, the first substrate with a photoresist mask of the nanochannel array is obtained.

Then the first substrate with the photoresist mask is etched to obtain a plurality of nanochannels on the surface of the first substrate thus forming the etched first substrate.

The etched first substrate is then immersed in an organic solvent or a photoresist remover to remove the photoresist mask on the surface of the etched first substrate thus obtaining the nanochannel array layer.

In one embodiment, the operation process of fabricating the plurality of nanochannels in the first substrate to obtain the nanochannel array layer is as follows.

A negative photoresist layer is coated on the surface of a template substrate. After soft baking, an exposure treatment is performed using a nanochannel mask. Then the exposed template substrate is subjected to a post-baking treatment. Next, the post-baked template substrate is immersed in a developer for development. After hard baking of the patterned photoresist film, the template substrate with a photoresist mold of the nanochannel array is obtained.

Then a PDMS mixed solution is cast over the template substrate with the photoresist mold of the nanochannel array. After a curing process, the PDMS replica is peeled off from the template substrate to obtain the first substrate with the nanochannel array, that is, the nanochannel array layer.

In one embodiment, the inlet microchannel array and/or the outlet microchannel array are created in the second substrate by etching, nanoimprinting, hot embossing lithography, soft photolithography based on the PDMS replica molding, injection moulding, 3D printing, or laser micromachining, etc.

In one embodiment, the input unit and the output unit are fabricated on the second substrate, where the input unit includes an inlet microchannel array and at least one inlet, and the output unit includes an outlet microchannel array and at least one outlet, and the operation process of obtaining the microchannel array layer is as follows.

A negative photoresist layer is coated on the surface of a template substrate. After soft baking, an exposure treatment is performed using a microchannel mask. Then the exposed template substrate is subjected to a post-baking treatment. Next, the post-baked template substrate is immersed in a developing solution for development. After hard baking of the patterned photoresist film, the template substrate with a photoresist mold of the microchannel array is obtained.

Then the PDMS mixed solution is poured on the template substrate with the photoresist mold of the microchannel array. After a curing process, the PDMS replica is peeled off from the photoresist mold to obtain the second substrate with the inlet microchannel array and/or the outlet microchannel array.

Then the second substrate with the inlet microchannel array and/or the outlet microchannel array is punched to make the at least one inlet and the at least one outlet thus obtaining the microchannel array layer.

In one embodiment, the input unit and the output unit are fabricated on the second substrate, where the input unit includes an inlet microchannel array and at least one inlet, and the output unit includes an outlet microchannel array and at least one outlet, and the operation process of obtaining the microchannel array layer is as follows.

A positive photoresist layer is coated on the surface of the second substrate. After soft baking, an exposure treatment is performed using a microchannel mask. Then the exposed second substrate is immersed in a developer solution for development. After hard baking of the patterned photoresist film, the second substrate with a photoresist mask of the microchannel array is obtained.

Then the second substrate with the photoresist mask is etched to fabricate a plurality of microchannels on the surface of the second substrate thus forming the etched second substrate.

After the etching, the second substrate with the inlet microchannel array and/or the outlet microchannel array is laser-punched to make the at least one inlet and the at least one outlet.

The punched second substrate is immersed in an organic solvent or a photoresist remover, so that the photoresist mask on the surface of the etched second substrate is removed to obtain the microchannel array layer.

In one embodiment, the at least one nanochannel array layer and the at least one microchannel array layer are alternately stacked and bonded by oxygen plasma bonding, anodic bonding, fusion bonding, low-temperature bonding, silicon wafer-to-wafer bonding, thermal bonding, or adhesive bonding, etc.

In one embodiment, the operation process of alternately stacking and bonding the at least one nanochannel array layer and the at least one microchannel array layer includes subjecting the top surface of the first substrate and the bottom surface of the second substrate to oxygen plasma treatment, and then aligning and bonding the top surface of the first substrate with the bottom surface of the second substrate.

There is further provided a method of preparing cargo-carrying biological particles, the method including the following operations:

injecting a mixed solution of a biological particle solution and a cargo solution into the at least one inlet of the micro- and nano-fluidic chip as recited in claim 1, where the biological particles include at least one of EVs, nanovesicles, membrane vesicles secreted by the microorganisms, subcellular particles with a size of 30 nm to 2000 nm and having a membrane structure, cell membrane nanoparticles with a size of 30 nm to 2000 nm, artificially synthesized nanoparticles with a size of 30 nm to 2000 nm wrapped in a phospholipid bilayer, liposomes with a diameter of 30 nm to 2000 nm, or viral vectors, etc.

where the mixed solution enters the at least one nanochannel through the at least one inlet microchannel, and because the depth, width, or diameter of the at least one nanochannel is less than or equal to the diameter of the biological particles, the membrane of the biological particles is mechanically squeezed in the at least one nanochannel so as to introduce pores, and the cargo molecules are convectively transported into the interior of the biological particles from the outside through the pores thus realizing the cargo-loading function; and collecting the chip-treated mixed solution from the at least one outlet of the micro- and nano-fluidic chip, and obtaining the cargo-carrying biological particles by a purification process.

In one embodiment, in the case where the biological particles are EVs, the preparation of the biological particle solution includes the following operations:

isolating EVs from a biological sample; and then
resuspending the EVs in a phosphate-buffered saline (PBS), cell culture medium, or normal saline, etc. to obtain the biological particle solution.

In one embodiment, in the operation of isolating the EVs from a biological sample, an ultracentrifugal isolation method, a density gradient centrifugal isolation method, a filtration isolation method, an immunocapture isolation method, a precipitation kit isolation method, a size-exclusion chromatography isolation method, a microfluidic-based isolation method, or a polymer precipitation isolation method, etc. is used.

In one embodiment, the biological sample is cell culture supernatant, plasma, serum, urine, saliva, cerebrospinal fluid, ascitic fluid, amniotic fluid, semen, synovial fluid, bronchial fluid, tears, bile, gastric acid, lymph, pleural effusion, gastrointestinal lavage fluid, bronchoalveolar lavage fluid, milk, grape, grapefruit, lemon, watermelon, carrot, ginger, tomato, broccoli, or *ginseng*, etc.

In one embodiment, the exogenous cargos in the cargo solution include at least one of drug cargos with a size of 500 nm or less, protein cargos with a size of 500 nm or less, nanomaterial cargos with a size of 500 nm or less, nucleic acid cargos with a size of 500 nm or less, or biomolecule cargos with a size of 500 nm or less, etc.

In one embodiment, the drug cargos with a size less than or equal to 500 nm include anticancer drugs, drugs for infectious diseases, drugs for cardiovascular diseases, drugs for neurodegenerative diseases, or drugs for autoimmune diseases, etc.

In one embodiment, the anticancer drugs include doxorubicin, curcumin, and paclitaxel, etc.

the drugs for infectious diseases include amphotericin B, ciprofloxacin, rifampicin, and tobramycin, etc.

the drugs for cardiovascular disease include amiodarone, atenolol, and isosorbide-5-mononitrate, etc.

the drugs for neurodegenerative disease include tanshinone IIA, levodopa, donepezil, and memantine, etc.

the drugs for autoimmune disease include tacrolimus and dexamethasone sodium phosphate, etc.

the protein cargos include immunoglobulin, interleukin, bovine serum albumin, endonuclease, and Cas9 protein, etc.

the nanomaterial cargos include quantum dots, carbon nanotubes, and nanoparticles, etc.

the nucleic acid cargos include plasmids, ribonucleic acids, deoxyribonucleic acids, and oligonucleotides, etc.

the biomolecule cargos include potassium ion probe molecules, calcium ion probe molecules, and inositol triphosphate, etc.

In one embodiment, the purification methods include ultracentrifugation, density gradient centrifugation, filtration, immunocapture, precipitation kit method, size-exclusion chromatography, microfluidic-based method, and polymer precipitation, etc.

There is further provided a method of preparing cargo-carrying biological particles, the method including the following operations:

injecting the solution of biological particles into the at least one inlet of the above-described micro- and nano-fluidic chip, where the biological particles include at least one of the EVs, nanovesicles, membrane vesicles secreted by the microorganisms, subcellular structure with a size of 30 nm to 2000 nm and having a membrane structure, cell membrane nanoparticles with a size of 30 nm to 2000 nm, artificially synthesized nanoparticles with a size of 30 nm to 2000 nm wrapped in a phospholipid bilayer, liposomes with a diameter of 30 nm to 2000 nm, or viral vectors, etc.

where the solution of biological particles enters the at least one nanochannel through the at least one inlet microchannel, and because the depth, width, or diameter of the at least one nanochannel is less than or equal to the diameter of the biological particles, the membrane of the biological particles is mechanically squeezed in the at least one nanochannel so as to introduce pores; and collecting the chip-treated solution of the biological particles from the at least one outlet of the micro- and nano-fluidic chip, and mixing the exogenous cargos with the squeezed biological particle solution, so that the cargo molecules diffuse into the interior of the biological particles from the outside through the pores, and further obtaining the cargo-carrying biological particles by the purification process.

Further disclosed are applications of the above-described micro- and nano-fluidic chip in squeezing biological particles for cargo loading, synthesizing liposomes and squeezing the liposomes for cargo loading, synthesizing cell membrane fragments into cell membrane nanoparticles and squeezing them for cargo loading, or the application in cargo loading of artificially synthesized nanoparticles that are wrapped by a phospholipid bilayer.

Further disclosed are applications of the above-described micro- and nano-fluidic chip that is fabricated using the above-mentioned method in squeezing biological particles for cargo loading, synthesizing liposomes and squeezing the liposomes for cargo loading, synthesizing cell membrane fragments into cell membrane nanoparticles and squeezing them for cargo loading, or the application in cargo loading of artificially synthesized nanoparticles that are wrapped by a phospholipid bilayer structure.

In the above-described micro- and nano-fluidic chip, the inlet microchannels and the outlet microchannels are connected to each other through the nanochannels, so that after the sample is injected into the nanochannels from the inlet microchannels, it will be mechanically squeezed by the nanochannels to reach the outlet microchannels. Since the depth, width or diameter of the nanochannels is similar to the size of biological particles, biological particles such as EVs ranging from 30 nm to 2000 nm can be effectively mechanically squeezed, so that the membrane of biological particles such as EVs can be permeabilized allowing for the loading of a variety of drug cargos, protein cargos, nanomaterial cargos, nucleic acid cargos, or biomolecule cargos with different sizes. Compared with the existing electroporation methods, the present disclosure not only avoids the use of an external electric field, but also avoids the problems of agglomeration and viability reduction of biological particles such as EVs. Because the need for special instruments for applying an electric field is eliminated, the cost is effectively reduced, which is helpful for technology promotion or industrial application. In addition, by providing multiple inlet microchannels, outlet microchannels and nanochannels, it has the advantage of high throughput, which can effectively increase the throughput of the cargo-loading process, and solves the problem of low cargo-loading efficiency in common incubation methods. The above-mentioned micro- and nano-fluidic chip can not only be used for cargo-loading research of biological particles such as EVs, but also has the potential to be promoted in clinical applications, so as to meet the needs of experimental research and clinical applications for NDSs.

The above-described method of fabricating the micro- and nano-fluidic chip is simple and straightforward to operate.

The above-mentioned method of preparing cargo-carrying biological particles is simple and straightforward to operate. The nanochannels can effectively mechanically squeeze the biological particles, so that the membrane of biological particles such as EVs can be permeabilized allowing for the loading of a variety of drug cargos, protein cargos, nanomaterial cargos, nucleic acid cargos, or biomolecule cargos with different sizes. Compared with the existing electroporation methods, the present disclosure not only avoids the use of an external electric field, but also avoids the problems of agglomeration and viability reduction of biological particles such as EVs. Because the need for special instruments for applying an electric field is eliminated, the cost is effectively reduced, which is helpful for technology promotion or industrial application.

BRIEF DESCRIPTION OF DRAWINGS

FIG. 15 is a schematic diagram illustrating the reaction mechanism of the method of preparing the cargo-carrying biological particles.

FIG. 16 is a flowchart of a method of preparing cargo-carrying biological particles according to another embodiment of this disclosure.

DETAILED DESCRIPTION

Figure 1A:
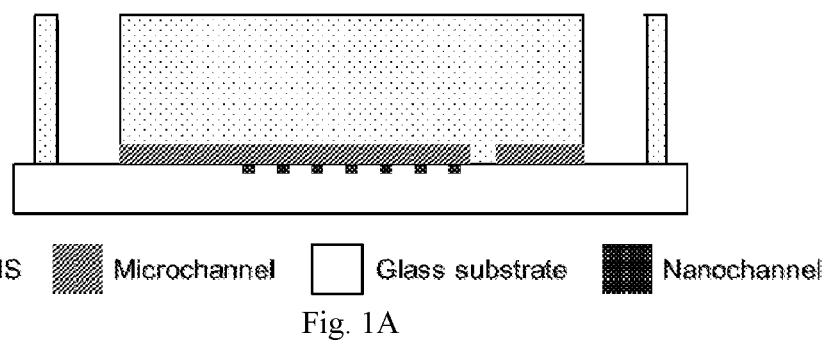
FIG. 1A is a front view of a micro- and nano-fluidic chip according to an embodiment of this disclosure.

For a better understanding of the objectives, technical solutions, and advantages of the present disclosure, hereinafter the present disclosure will be described in further detail in connection with the accompanying drawings and some illustrative embodiments. It is to be understood that the specific embodiments described here are intended for the mere purposes of illustrating this disclosure, instead of limiting. As used herein, a "fixed connection" includes a direct fixed connection and an indirect fixed connection.

The biological particles in this application refer to the EVs, nanovesicles, membrane vesicles secreted by the microorganisms, subcellular particles having a membrane structure, cell membrane nanoparticles, artificially synthesized nanoparticles wrapped in a phospholipid bilayer, liposomes that have a size of 30 nm to 2000 nm, or viral vectors, etc.

As illustrated in FIG. 1A-FIG. 1C and FIG. 2A-FIG. 2C, the micro- and nano-fluidic chip according to one embodiment includes at least one nanochannel array layer 30 and at least one microchannel array layer 40. The nanochannel array layer 30 and the microchannel array layer 40 are alternately stacked.

The nanochannel array layer 30 includes at least one nanochannel 32.

The microchannel array layer 40 includes an input unit and an output unit. The input unit includes an inlet microchannel array and at least one inlet 10, and the output unit includes an outlet microchannel array and at least one outlet 20. The inlet microchannel array includes at least one inlet microchannel 42, and the outlet microchannel array includes at least one outlet microchannel 46, where the at least one inlet microchannel 42 and the at least one microchannel 46 are alternately arranged at intervals. The at least one inlet 10 is connected to the at least one inlet microchannel 42, and the at least one outlet 20 is connected to the at least one outlet microchannel 46. Each pair of inlet microchannel 42 and outlet microchannel 46 are bridged by the at least one nanochannel 32.

Figure 1B:
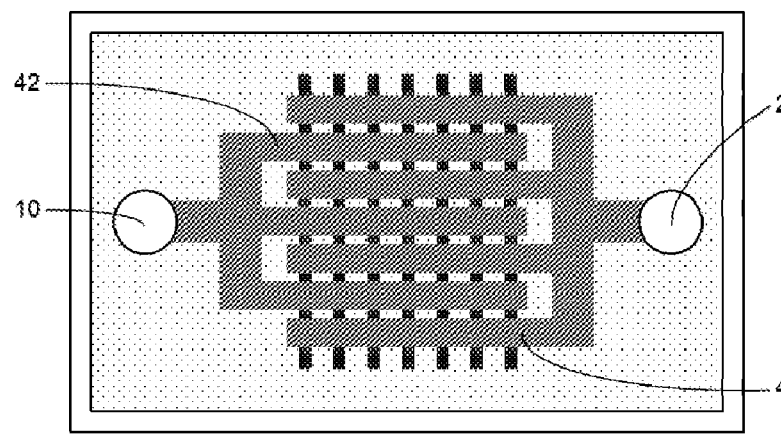
FIG. 1B is a top view of the micro- and nano-fluidic chip shown in FIG. 1A.
Figure 1C:
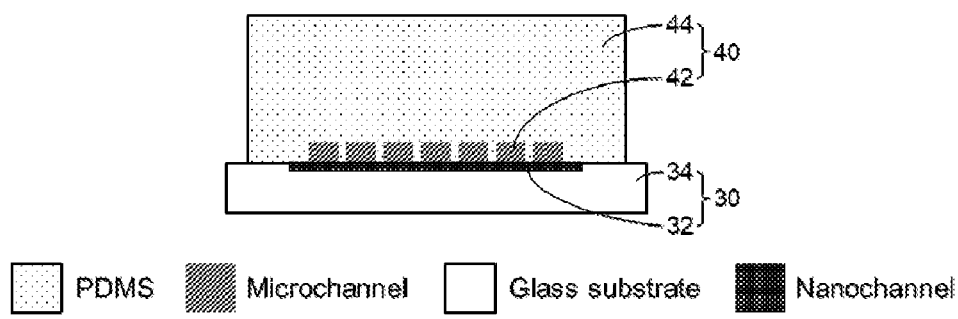
FIG. 1C is a left side view of the micro- and nano-fluidic chip shown in FIG. 1A.

As illustrated in FIG. 1A-FIG. 1C, when the microchannel array layer 40 is one layer, the microchannel array layer 40 includes an input unit and an output unit. When the nanochannels 32 connects the microchannels 42 and the microchannels 46, the extension direction of the nanochannels 32 is set at an angle of 0°~90° with the microchannel array layer 40.

Figure 2A:
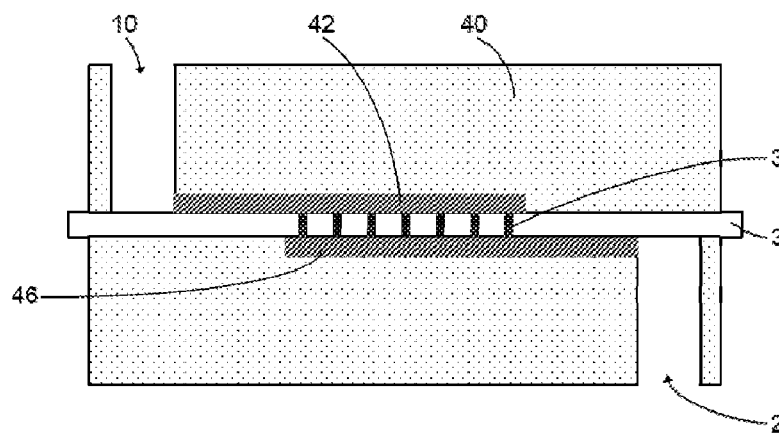
FIG. 2A is a front view of a micro- and nano-fluidic chip according to another embodiment of this disclosure.
Figure 2B:
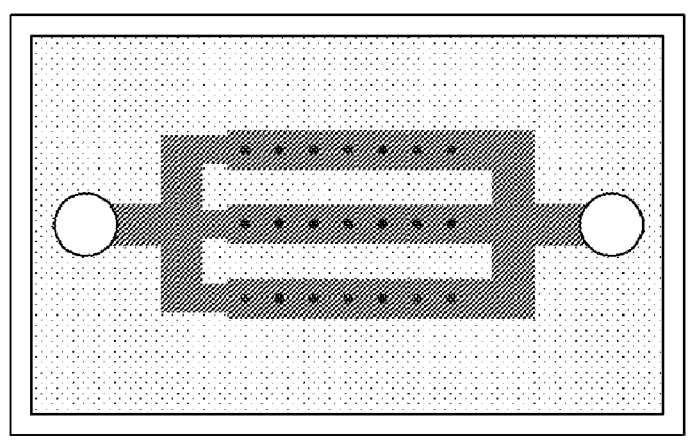
FIG. 2B is a top view of the micro- and nano-fluidic chip shown in FIG. 2A.
Figure 2C:
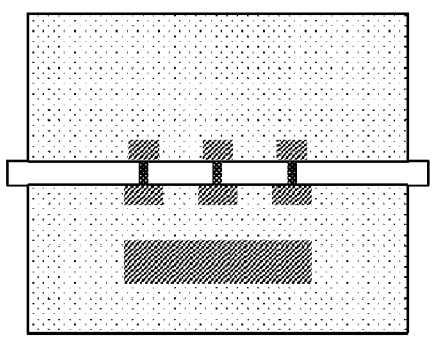
FIG. 2C is a left side view of the micro- and nano-fluidic chip shown in FIG. 2A.

Now referring to FIG. 2A-FIG. 2C, when the microchannel array layer 40 has two or more layers, one of the microchannel array layers 40 includes the input unit, and the other microchannel array layer 40 includes the output unit. The nanochannel array layer 30 is arranged between the two adjacent microchannel array layers 40. When the at least one nanochannel 32 connects the at least one inlet microchannel 42 to the at least one outlet microchannel 46, the extension direction of the at least one nanochannel 32 is set at an angle of 0°~90° with the microchannel array layer 40.

In particular, in the embodiment illustrated in FIG. 2A-FIG. 2C, the microchannel array layer 40 includes two layers. In the above-described micro- and nano-fluidic chip, the inlet microchannels 42 and the outlet microchannels 46 are connected to each other through the nanochannels 32, so that after the sample is injected into the nanochannels 32 from the inlet microchannels 42, it will be mechanically squeezed by the nanochannels 32 to reach the outlet microchannels 46. Since the depth, width or diameter of the nanochannels 32 is similar to the size of biological particles, the biological particles such as EVs can be effectively mechanically squeezed, so that the membrane of biological particles can be permeabilized allowing for the loading of a variety of drug cargos, protein cargos, nanomaterial cargos, nucleic acid cargos, or biomolecule cargos with different sizes. Compared with the existing electroporation methods, the present disclosure not only avoids the use of an external electric field, but also avoids the problems of agglomeration and viability reduction of biological particles such as EVs. Because the need for special instruments for applying an electric field is eliminated, the cost is effectively reduced, which is helpful for technology promotion or industrial application. In addition, by providing multiple inlet microchannels 42, outlet microchannels 46 and nanochannels 32, it has the advantage of high throughput, which can effectively increase the throughput of the cargo-loading process, and solves the problem of low cargo-loading efficiency in common incubation methods. The above-mentioned micro- and nano-fluidic chip can not only be used for cargo-loading research of biological particles such as EVs, but also has the potential to be promoted in clinical applications, so as to meet the needs of experimental research and clinical applications for NDSs.

In the embodiment illustrated in FIG. 1A-FIG. 1C, the substrate of the nanochannel array layer 30 is a glass substrate 34. It will be appreciated that the material of the nanochannel array layer 30 will not be limited to glass, and it may also be PDMS, quartz, silicon wafer, silicon wafer, silicon nitride wafer, silicon dioxide wafer, silicon carbide wafer, PMMA, parylene-C, PC, COC, COP, PP, photocurable resin, sTPE, or other commonly used micro- and nano-processing materials.

In the embodiment illustrated in FIG. 1A-FIG. 1C, the material of the microchannel array layer 40 is PDMS 44. It will be appreciated that the material of the microchannel array layer 40 will not be limited to PDMS, and it may also be glass, quartz, silicon wafer, silicon wafer, silicon nitride wafer, silicon dioxide wafer, silicon carbide wafer, PMMA, parylene-C, PC, COC, COP, PP, photocurable resin, sTPE, or other commonly used micro- and nano-processing materials.

The nanochannel array layer 30 and the microchannel array layer 40 will not be limited to be separately disposed in the upper and lower substrates; they may also be disposed in the same substrate.

In the embodiment illustrated in FIG. 1A-FIG. 1C, each of the nanochannel array layer 30 and the microchannel array layer 40 has only one layer. It will be appreciated that the micro- and nano-fluidic chip will also not be limited to two layers, and can be expanded into multiple layers, as long as there is arranged a nanochannel array layer 30 between any two microchannel array layers 40 for connection.

In the case where the nanochannel array includes at least two nanochannels, the nanochannels of the nanochannel array layer may be arranged at an angle of 0° to 90° with respect to each other. In the embodiment illustrated in FIG. 1A-FIG. 1C, the nanochannels 32 of the nanochannel array layer 30 are arranged in parallel. It will be appreciated that the nanochannels 32 don't need to be arranged completely in parallel, as long as the nanochannels 32 are operative to connect the inlet microchannels 42 and the outlet microchannels 46. For example, in the embodiment illustrated in FIG. 7A-FIG. 7C, the nanochannels intersect each other at an angle of 0° to 90°.

Figure 3A:
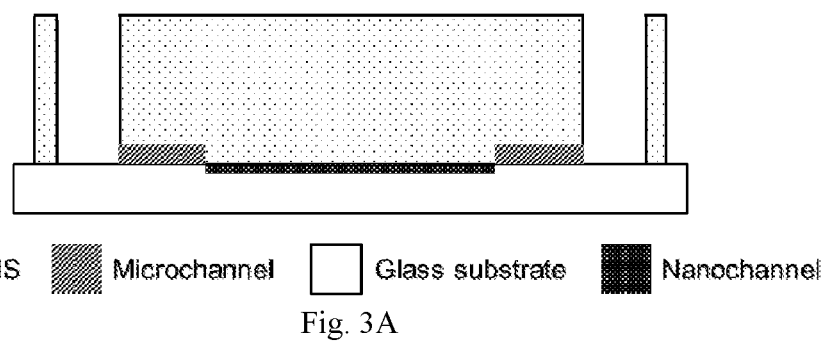
FIG. 3A is a front view of a micro- and nano-fluidic chip according to yet another embodiment of this disclosure.
Figure 3B:
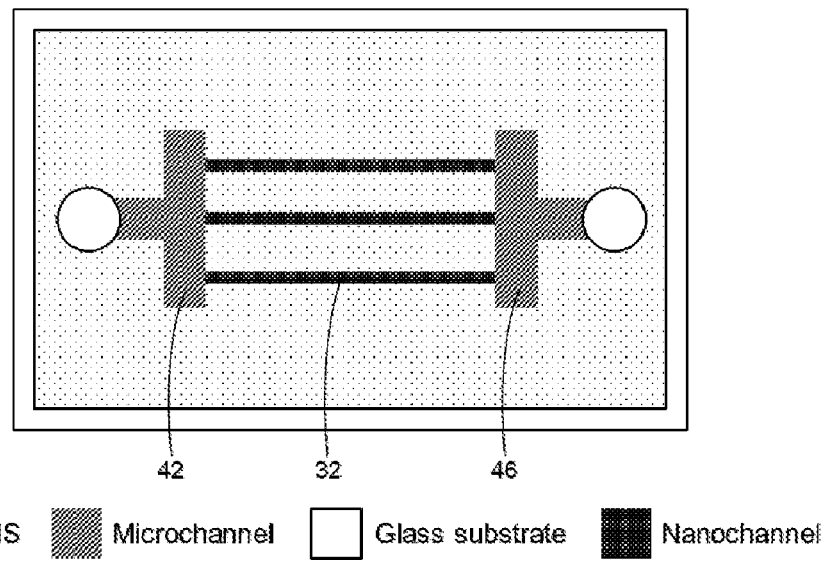
FIG. 3B is a top view of the micro- and nano-fluidic chip shown in FIG. 3A.
Figure 3C:
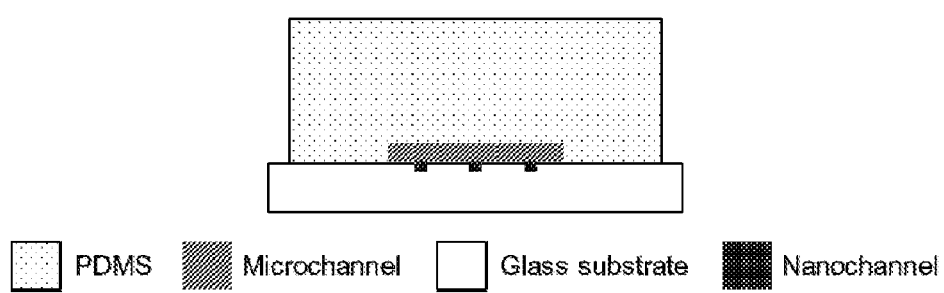
FIG. 3C is a left side view of the micro- and nano-fluidic chip shown in FIG. 3A.

Now referring to FIG. 3A-FIG. 3C, in the case where there is provided one of the inlet microchannels 42 and one of the outlet microchannels 46, the inlet microchannel 42 and the outlet microchannel 46 may be arranged in parallel. It will be appreciated that the inlet microchannel 42 and the outlet microchannel don't need to be arranged in parallel, and they may be arranged at an angle of 0° to 90°. In FIG. 3A-FIG. 3C, there are provided three of the nanochannels 32. It will be appreciated however that it will not be limited to three in practice, but the number of nanochannels 32 is at least one.

In the case where there are two or more of the inlet microchannels and two or more of the outlet microchannels, as is the case in the embodiment illustrated in FIG. 1A-FIG. 1C, the inlet 10 is connected to the inlet microchannels 42 through the inlet connecting channel. In particular, the inlet 10 is connected to the inlet connecting channel. The plurality of inlet microchannels 42 are arranged in parallel and one end of the plurality of inlet microchannels 42 is connected to the inlet connecting channel. The outlet 20 is connected to the outlet microchannels 46 through an outlet connecting channel. In particular, the outlet 20 is connected to the outlet connecting channel. The plurality of outlet microchannels 46 are arranged in parallel and one end of the multiple outlet microchannels 46 is connected to the outlet connecting channel. The inlet microchannels 42 and the outlet microchannels 46 are alternately arranged at intervals. It can be understood that the inlet microchannels 42 and the outlet microchannels 46 don't have to be arranged completely in parallel, as long as the inlet microchannels 42 and the outlet microchannels 46 are spaced apart from each other.

Further, in the embodiment illustrated in FIG. 1A-FIG. 1C and FIG. 2A-FIG. 2C, the extension direction of the nanochannels 32 is perpendicular to the extension direction of the inlet microchannels 42 and the outlet microchannels 46. It will be appreciated that the extension direction of the nanochannels 32 will not be limited to being perpendicular to the extension direction of the inlet microchannels 42 and the outlet microchannels 46, and they may be arranged at an angle of 0°~90°, as long as the nanochannels 32 are operative to connect the inlet microchannels 42 and the outlet microchannels 46.

Figure 4A:
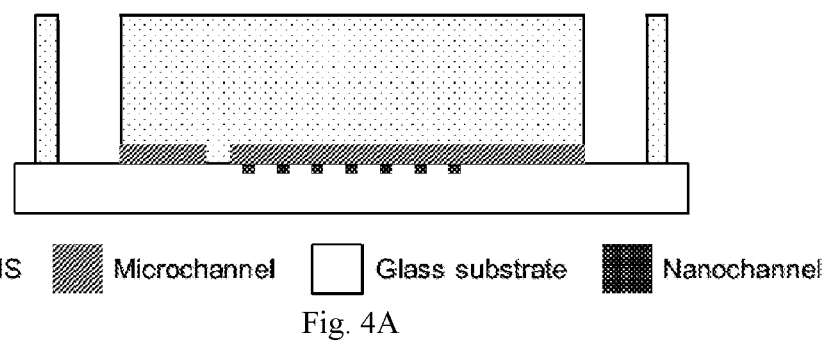
FIG. 4A is a front view of a micro- and nano-fluidic chip according to still another embodiment of this disclosure.
Figure 4B:
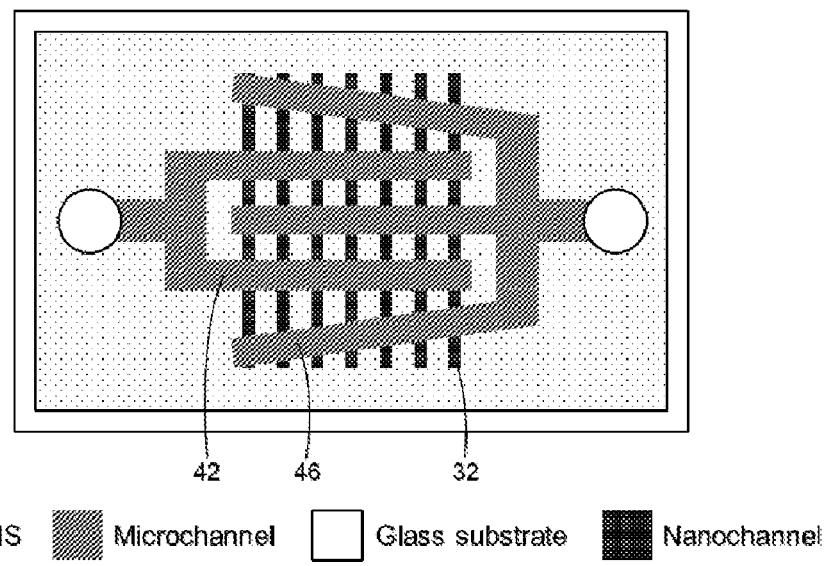
FIG. 4B is a top view of the micro- and nano-fluidic chip shown in FIG. 4A.
Figure 4C:
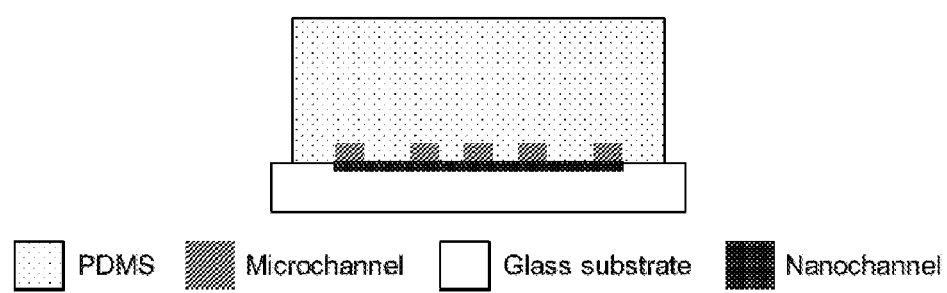
FIG. 4C is a left side view of the micro- and nano-fluidic chip shown in FIG. 4A.

In the embodiment illustrated in FIG. 1A-FIG. 1C, the inlet microchannels 42 are arranged in parallel, the outlet microchannels 46 are arranged in parallel, and the inlet microchannels 42 and the outlet microchannels 46 form a parallel interdigitated structure. Understandably, referring to FIG. 4A-FIG. 4C, the inlet microchannels 42 may be arranged at an angle of 0° ~ 90°, and the outlet microchannels 46 may be arranged at an angle of 0°~90°, and the inlet microchannels 42 and the outlet microchannels 46 may form an oblique interdigitated layout. The nanochannels 32 connect the inlet microchannels 42 and the outlet microchannels 46.

Figure 5A:
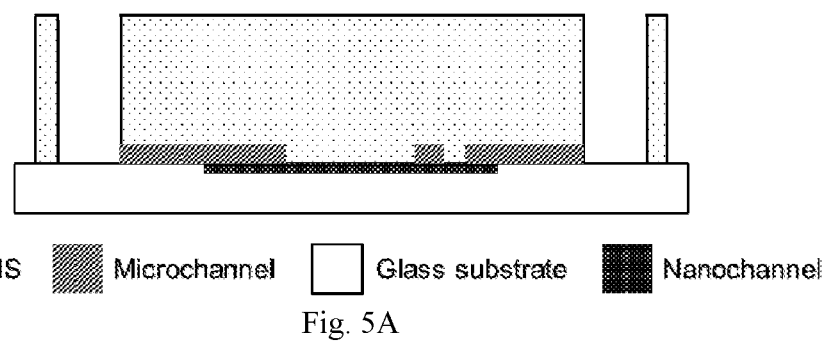
FIG. 5A is a front view of a micro- and nano-fluidic chip according to still another embodiment of this disclosure.
Figure 5B:
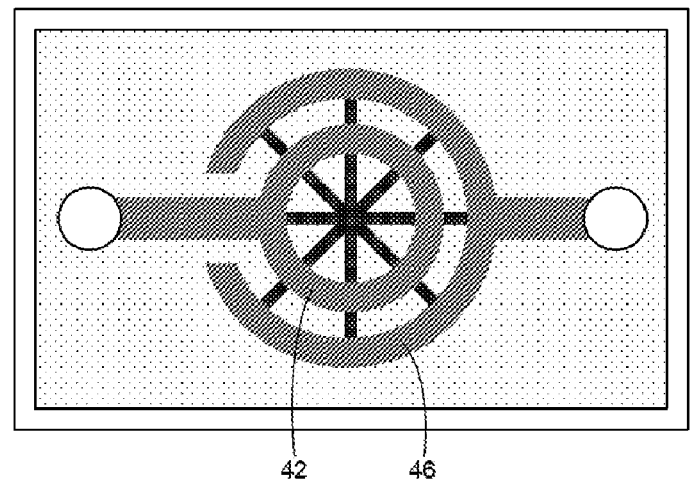
FIG. 5B is a top view of the micro- and nano-fluidic chip shown in FIG. 5A.
Figure 5C:
FIG. 5C is a left side view of the micro- and nano-fluidic chip shown in FIG. 5A.

In other embodiments, the inlet microchannels 42 and the outlet microchannels 46 may also have other shapes. For example, referring to FIG. 5A-FIG. 5C, the inlet microchannels 42 have a circular shape, the outlet microchannels 46 have an annular shape, and the inlet microchannels 42 and the outlet microchannels 46 form a circular interdigitated layout.

Figure 6A:
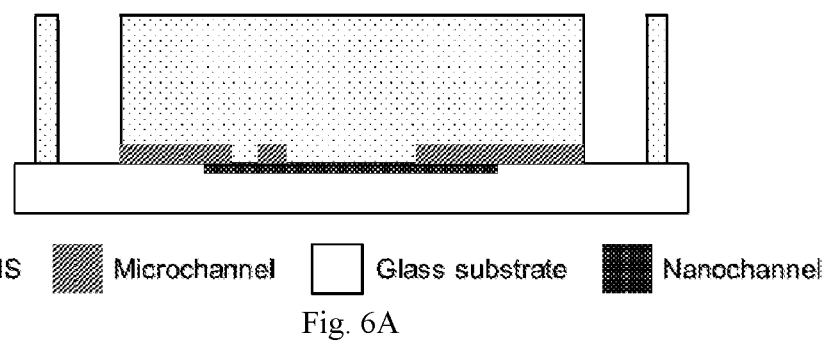
FIG. 6A is a front view of a micro- and nano-fluidic chip according to still another embodiment of this disclosure.
Figure 6B:
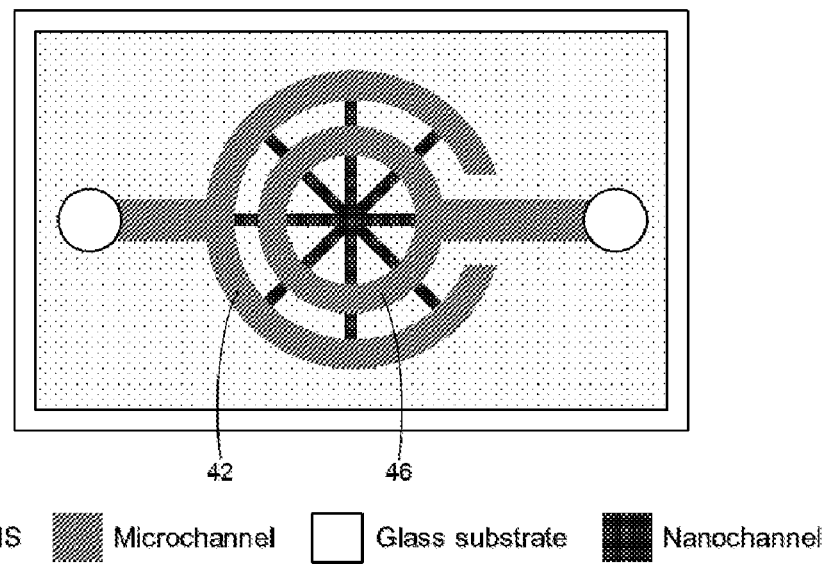
FIG. 6B is a top view of the micro- and nano-fluidic chip shown in FIG. 6A.
Figure 6C:
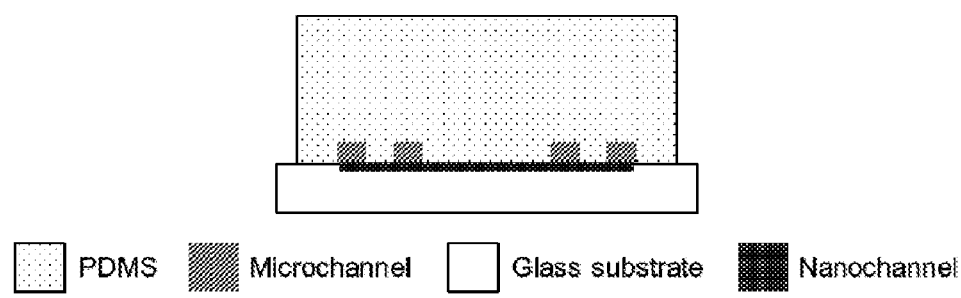
FIG. 6C is a left side view of the micro- and nano-fluidic chip shown in FIG. 6A.

Now referring to FIG. 6A-FIG. 6C, in another embodiment, the inlet microchannels 42 have an annular shape, the outlet microchannels 46 have a circular shape, and the inlet microchannels 42 and the outlet microchannels 46 form a circular interdigitated layout.

Figure 7A:
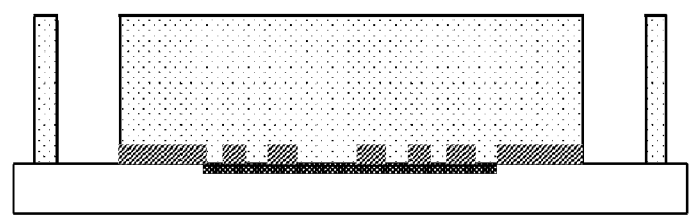
FIG. 7A is a front view of a micro- and nano-fluidic chip according to still another embodiment of this disclosure.
Figure 7B:
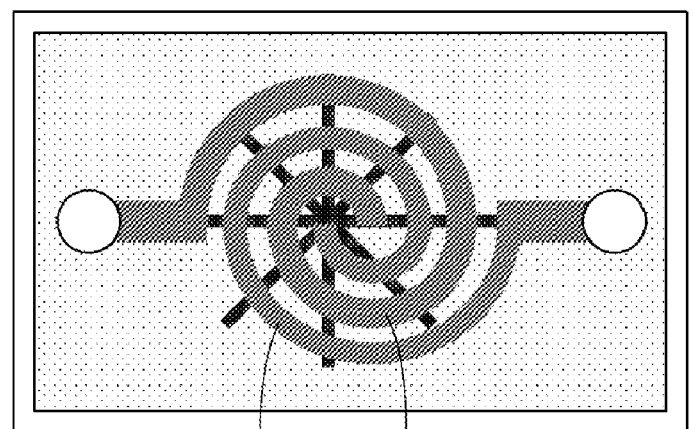
FIG. 7B is a top view of the micro- and nano-fluidic chip shown in FIG. 7A.
Figure 7C:
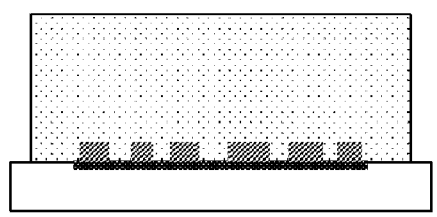
FIG. 7C is a left side view of the micro- and nano-fluidic chip shown in FIG. 7A.

Now referring to FIG. 7A-FIG. 7C, in another embodiment, the inlet microchannels 42 have a spiral shape, the outlet microchannels 46 have a spiral shape, and the inlet microchannels 42 and the outlet microchannels 46 form a spiral interdigitated layout.

In one embodiment, the inlet microchannels 42 have a depth of 1 μm to 1000 μm, and the outlet microchannels 46 have a depth of 1 μm to 1000 μm. In the case where the nanochannels 32 have a rectangular parallelepiped shape, the nanochannels 32 have a depth of 10 nm to 5000 nm, and a width of 10 nm to 1000 μm. In the case where the nanochannels 32 have a cylindrical shape, the nanochannels 32 have a diameter of 10 nm to 5000 nm. It will be appreciated that in actual operation, the width, depth, length, and spacing of the nanochannels 32 may be designed to be of different sizes, as long as the micro- and nano-fluidic chip is operative to process biological particles with different sizes. For example, exosomes with a size of 30 nm~ 200 nm, microvesicles with a size of 200 nm~ 2000 nm, apoptotic bodies with a size of 500 nm~2000 nm, nanovesicles with a size of 30 nm~2000 nm, subcellular particles with a size of 30 nm~ 2000 nm, cell membrane nanoparticles with a diameter of 30 nm~ 2000 nm, artificially synthesized nanoparticles with a size of 30 nm~ 2000 nm that are wrapped in a phospholipid bilayer, or liposomes with a diameter of 30 nm~2000 nm, etc.

It can be understood that the number of inlet microchannels 42, outlet microchannels 46, and nanochannels 32 will not be limited, and different channel numbers may be set according to the throughput requirements of the micro- and nano-fluidic chip.

It is to be understood that the length, width, depth, and spacing of the inlet microchannels 42 and the outlet microchannels 46 will not be limited to a specific size, they are possible as long as a certain volume of mixed solution with the biological particles is able to be injected into the nanochannels 32.

It is to be understood that the inlet of the micro- and nano-fluidic chip will not be limited to one, and multiple inlets may be designed which respectively lead to a biological particle solution such as EV solution, a drug cargo solution, a protein cargo solution, a nanomaterial solution, a nucleic acid solution, or a biomolecular cargo solution.

It is to be understood that the outlet of the micro- and nano-fluidic chip will not be limited to one, and multiple outlets can be designed which may be used to separately collect cargo-carrying biological particles.

Figure 8:
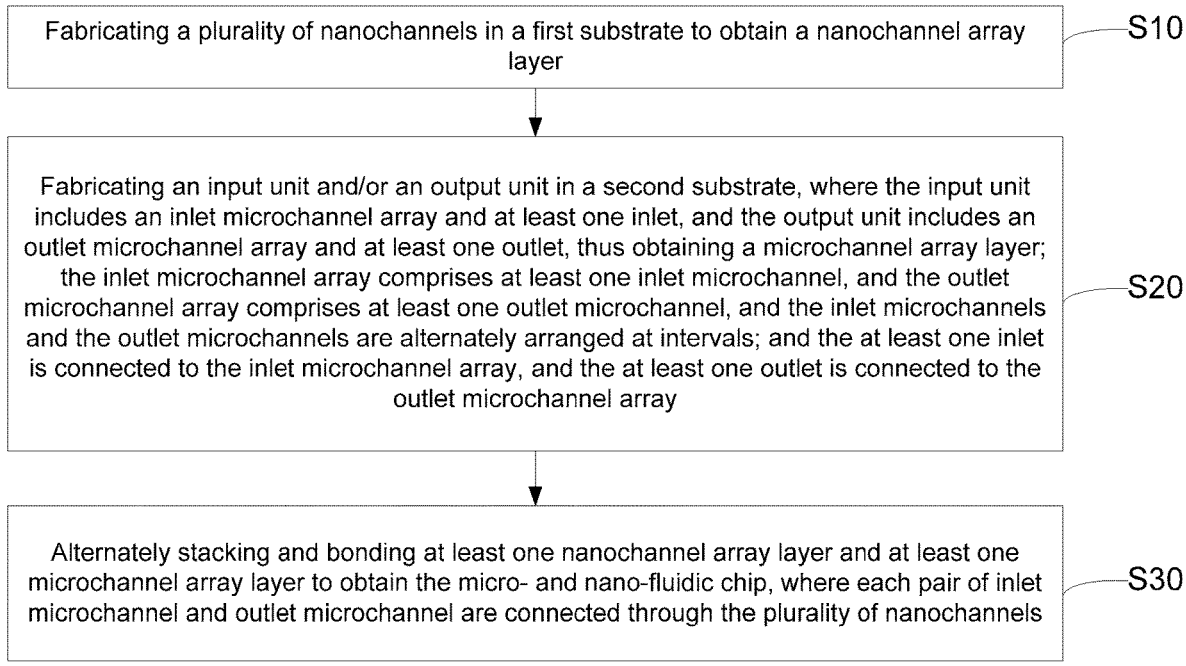
FIG. 8 is a flowchart of a method of fabricating a micro- and nano-fluidic chip according to an embodiment of this disclosure.

Now referring to FIG. 8, there is provided a method for fabricating the above-mentioned micro- and nano-fluidic chip, the fabrication method including the following operations S10, S20, and S30.

In S10, the method includes fabricating a plurality of nanochannels in the first substrate to obtain the nanochannel array layer.

It will be appreciated that in S10, the plurality of nanochannels may be formed in the first substrate by the etching, nanoimprinting, hot embossing lithography, soft photolithography based on PDMS replica molding, injection moulding, 3D printing, or laser micromachining, etc.

It will be appreciated that the material of the first substrate will not be limited to glass, and it may also be PDMS, quartz, silicon wafer, silicon nitride wafer, silicon dioxide wafer, silicon carbide wafer, PMMA, parylene-C, PC, COC, COP, PP, photocurable resin, sTPE, or other commonly used micro- and nano-processing materials.

In particular, in S10, the nanochannel array may be fabricated on the top of glass or other materials by using the etching method, or the nanochannel array may be fabricated on the top of the material such as PDMS by the soft photolithography method based on PDMS replica molding, or the nanochannel array may be fabricated on top of material such as PMMA using the nanoimprinting method, or the nanochannel array may be fabricated on the top of material such as photocurable resin using the 3D printing.

In S20, the method includes fabricating an input unit and/or an output unit on the second substrate, where the input unit includes an inlet microchannel array and at least one inlet, and the output unit includes an outlet microchannel array and at least one outlet, thereby obtaining a microchannel array layer. The inlet microchannel array includes at least one inlet microchannel, the outlet microchannel array includes at least one outlet microchannel, and the inlet microchannels and the outlet microchannels are alternately arranged at intervals. The at least one inlet is connected to the inlet microchannel array, and the at least one outlet is connected to the outlet microchannel array.

It will be appreciated that the material of the second substrate will not be limited to PDMS, and it may also be glass, quartz, silicon wafer, silicon nitride wafer, silicon dioxide wafer, silicon carbide wafer, PMMA, parylene-C, PC, COC, COP, PP, photocurable resin, sTPE, or other commonly used micro- and nano-processing materials.

It will be appreciated that in S20, the inlet microchannel array and/or the outlet microchannel array may be fabricated on the second substrate by etching, nanoimprinting, hot embossing lithography, soft photolithography based on PDMS replica molding injection moulding, 3D printing, or laser micromachining, etc. That is, the inlet microchannel array and the outlet microchannel array are fabricated on the second substrate. Alternatively, only the inlet microchannel array is fabricated on the second substrate, and the outlet microchannel array is not fabricated. Alternatively, only the outlet microchannel array is fabricated on the second substrate, and the inlet microchannel array is not fabricated.

Now referring to FIG. 8, in the case where only the inlet microchannel array or the outlet microchannel array is fabricated on the second substrate, the corresponding outlet microchannel array or inlet microchannel array needs to be fabricated on a third substrate.

In particular, in S20, the soft photolithography method based on PDMS replica molding may be used to fabricate the microchannel array on the bottom of material such as PDMS, or the etching method may be used to etch the microchannel array on the bottom of material such as glass, or a nanoimprint method may be used to fabricated a microchannel array on the bottom of material such as PMMA, or the nanochannel array may be fabricated on the bottom of material such as photocurable resin using the 3D printing.

In S30, the method includes alternately stacking and bonding the least one nanochannel array layer and at least one microchannel array layer to obtain the micro- and nano-fluidic chip, wherein each pair of inlet microchannel and outlet microchannel are connected through the plurality of nanochannels.

It is to be understood that in S30, the at least one nanochannel array layer and the at least one microchannel array layer are alternately stacked and bonded by oxygen plasma bonding, anodic bonding, fusion bonding, or low-temperature bonding, silicon wafer-to-wafer bonding, thermal bonding, or adhesive bonding, etc.

Figure 9:
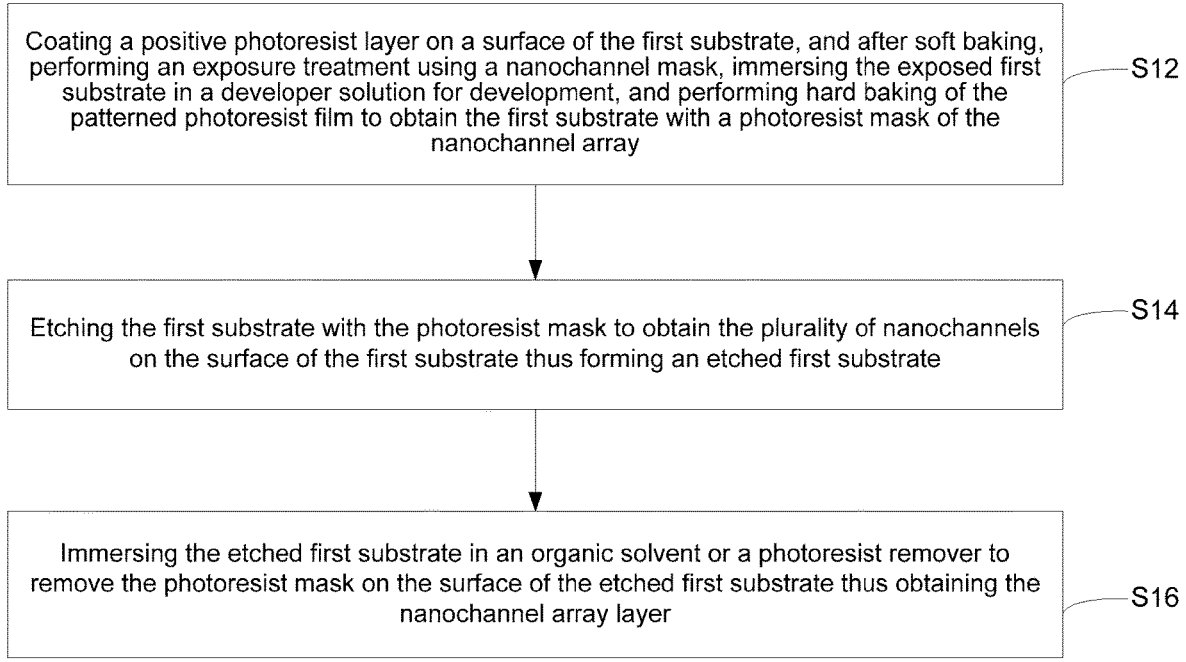
FIG. 9 is a flowchart of a method of fabricating a nanochannel array layer according to an embodiment of this disclosure.

In particular, in one embodiment, referring to FIGS. 9 and 12, in S10, the operation of fabricating a plurality of nanochannels in the first substrate to obtain a nanochannel array layer is as follows.

In S12, a positive photoresist layer is coated on the surface of the first substrate. After soft baking, an exposure treatment is performed using a nanochannel mask as illustrated by e in FIG. 12. Then the exposed first substrate is immersed in a developer solution for development, and the patterned photoresist film on the developed first substrate is hard baked to obtain the first substrate with a photoresist mask of the nanochannel array, as illustrated by f in FIG. 12.

In one embodiment, the first substrate may be a glass substrate.

In one embodiment, before the positive photoresist layer is coated on the surface of the first substrate, the first substrate may be cleaned and dried, and then the surface of the first substrate may be hydrophilized.

In an embodiment, a spin coating method may be used to coat the surface of the first substrate to form the positive photoresist layer.

The purpose of the soft baking is to remove the solvent in the positive photoresist layer and improve the adhesion of the photoresist to the first substrate.

The hard-baking operation includes baking the photoresist mask at a temperature of 90° C. to 130° C. for 5 minutes to 120 minutes to harden the photoresist and improve the adhesion of the photoresist to the first substrate.

Figure 12:
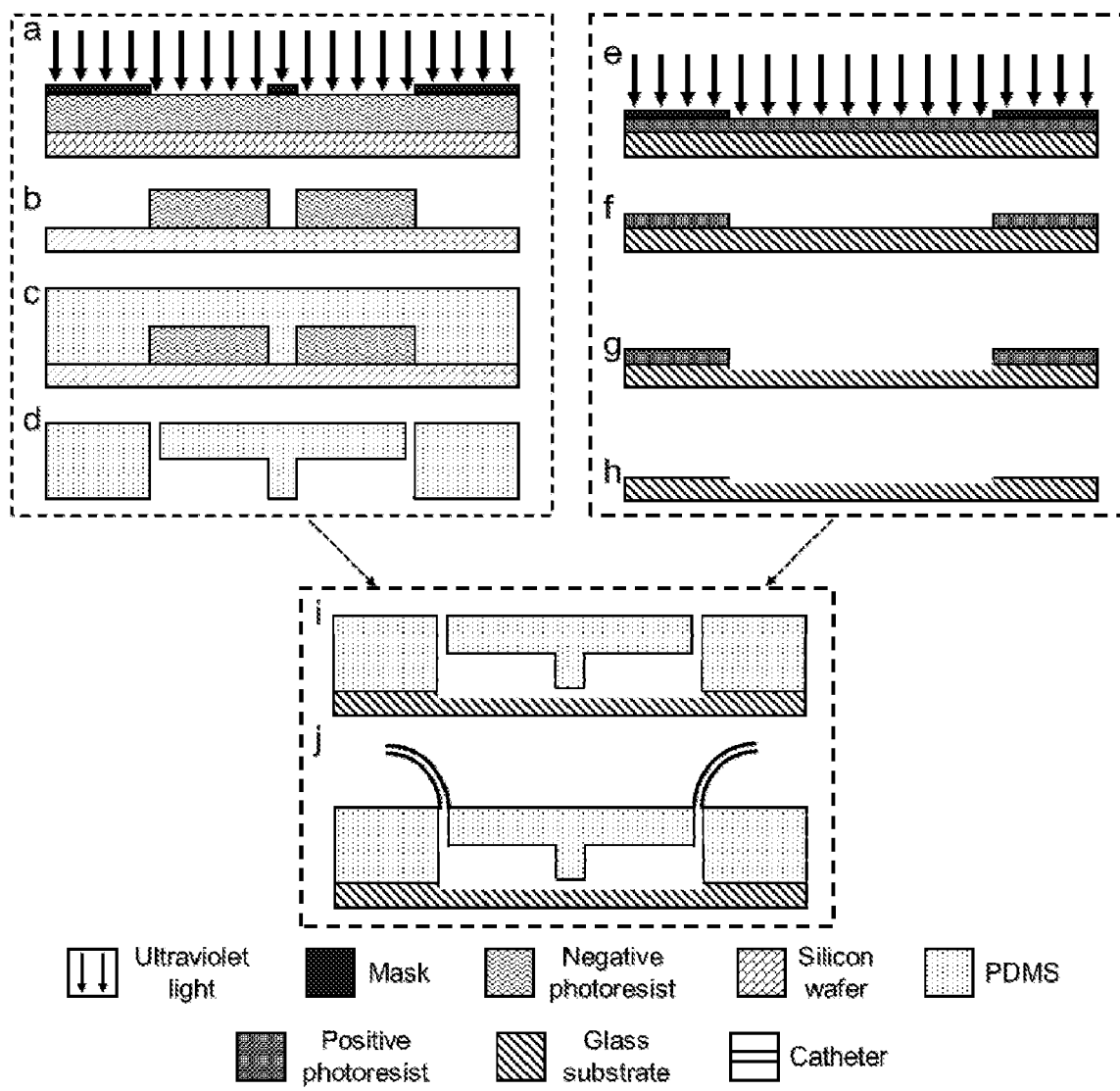
FIG. 12 is a schematic diagram illustrating a method of fabricating the micro- and nano-fluidic chip.

In S14, the first substrate with the photoresist mask is etched to obtain a plurality of nanochannels on the surface of the first substrate thus forming the etched first substrate, as illustrated by g in FIG. 12.

In S16, the etched first substrate is then immersed in an organic solvent or a photoresist remover to remove the photoresist mask on the surface of the etched first substrate thus obtaining the nanochannel array layer, as illustrated by h in FIG. 12.

That is, in S16, after removing the photoresist mask on the surface of the etched first substrate, a drying operation may be performed.

Figure 10:
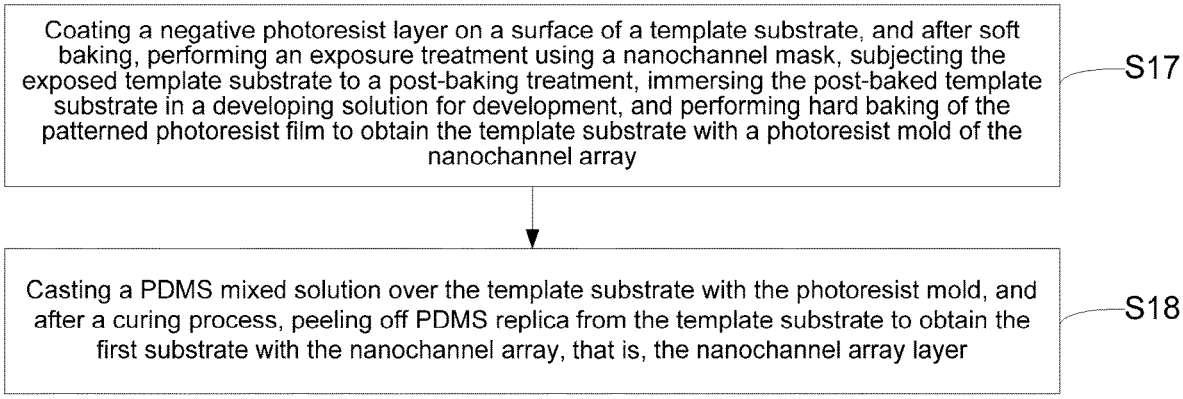
FIG. 10 is a flowchart of a method of fabricating a nanochannel array layer according to another embodiment of this disclosure.

In particular, in another embodiment, referring to FIG. 10, the operation of fabricating a plurality of nanochannels in the first substrate to obtain a nanochannel array layer may be as follows.

In S17, a negative photoresist layer is coated on the surface of a template substrate. After soft baking, an exposure treatment is performed using a nanochannel mask. Then the exposed template substrate is subjected to a post-baking treatment. Next, the post-baked template substrate is immersed in a developing solution for development, and the patterned photoresist film on the developed template substrate is hard baked to obtain the template substrate with a photoresist mold of the nanochannel array.

In S18, then a PDMS mixed solution is cast over the template substrate with the photoresist mold of the nanochannel array. After a curing process, the PDMS replica is peeled off from the template substrate to obtain the first substrate with the nanochannel array, that is, the nanochannel array layer.

Figure 11:
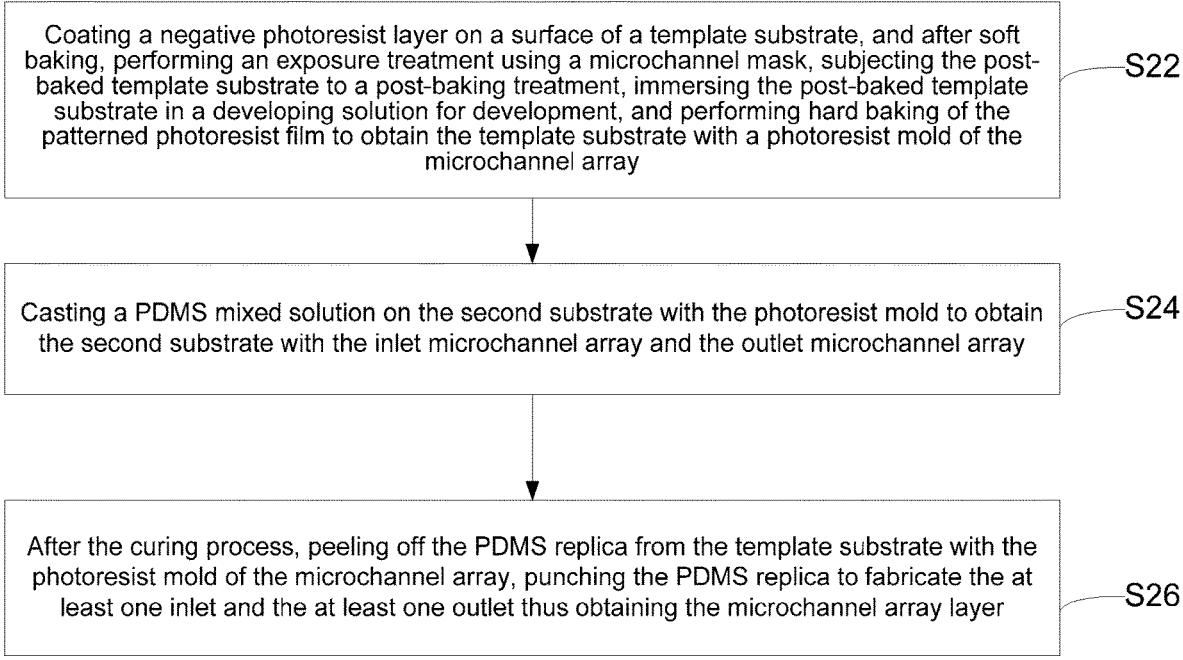
FIG. 11 is a flowchart of a method of fabricating a microchannel array layer according to an embodiment of this disclosure.

In particular, in one embodiment, as illustrated by FIG. 11, in S20, the input unit and the output unit are formed on the second substrate, where the input unit includes an inlet microchannel array and at least one inlet, and the output unit includes an outlet microchannel array and at least one outlet, and the operation of fabricating the microchannel array layer is as follows.

In S22, a negative photoresist layer is coated on the surface of the template substrate. After soft baking, an exposure treatment is performed using a microchannel mask as illustrated by a in FIG. 12. Then the exposed template substrate is subjected to a post-baking treatment. Next, the post-baked template substrate is immersed in a developer solution for development, and the patterned photoresist film on the developed template substrate is hard baked to obtain the template substrate with a photoresist mold of the microchannel array, as illustrated by b in FIG. 12.

In one embodiment, the template substrate may be a silicon wafer substrate.

In one embodiment, before the negative photoresist layer is coated on the surface of the template substrate, the template substrate is first cleaned and dried, and then the surface of the template substrate is hydrophilized. The photoresist is applied by spin coating method.

In one embodiment, after the exposure process is performed using the microchannel mask, a post-baking process is further included.

The purpose of the soft baking is to remove the solvent in the negative photoresist layer and improve the adhesion of the photoresist to the template substrate.

The purpose of post baking is to increase the strength of the negative photoresist in the exposed portions so as to improve the photolithography accuracy.

The hard-baking operation includes baking the photoresist mold at a temperature of 150° C. to 250° C. for 5 minutes to 120 minutes to harden the photoresist and improve the adhesion of the photoresist to the template substrate.

In S24, a PDMS mixed solution is cast over the template substrate with the photoresist mold of the microchannel array to obtain the second substrate with the inlet microchannel array and the outlet microchannel array, as illustrated by c in FIG. 12.

The PDMS mixed solution may be prepared by the following method: the PDMS curing agent and the PDMS prepolymer are mixed in a mass ratio of ⅓ to ¹/₁₂ and stirred uniformly to obtain the PDMS mixed solution.

In one embodiment, before casting the PDMS mixed solution, the photoresist mold of the microchannel array may be pretreated with a release agent. After casting the PDMS mixed solution over the photoresist mold, the PDMS mixed solution may be further baked at a certain temperature to make it cure.

In S26, after the curing process, the PDMS replica is peeled off from the template substrate with the photoresist mold of the microchannel array. Then the PDMS replica with the inlet microchannel array and the outlet microchannel array is punched to fabricate the at least one inlet and the at least one outlet to obtain the microchannel array layer, as illustrated by d in FIG. 12.

In one embodiment, after the PDMS mold is peeled off from the second substrate, a hole puncher is used to punch the holes.

Figure 13:
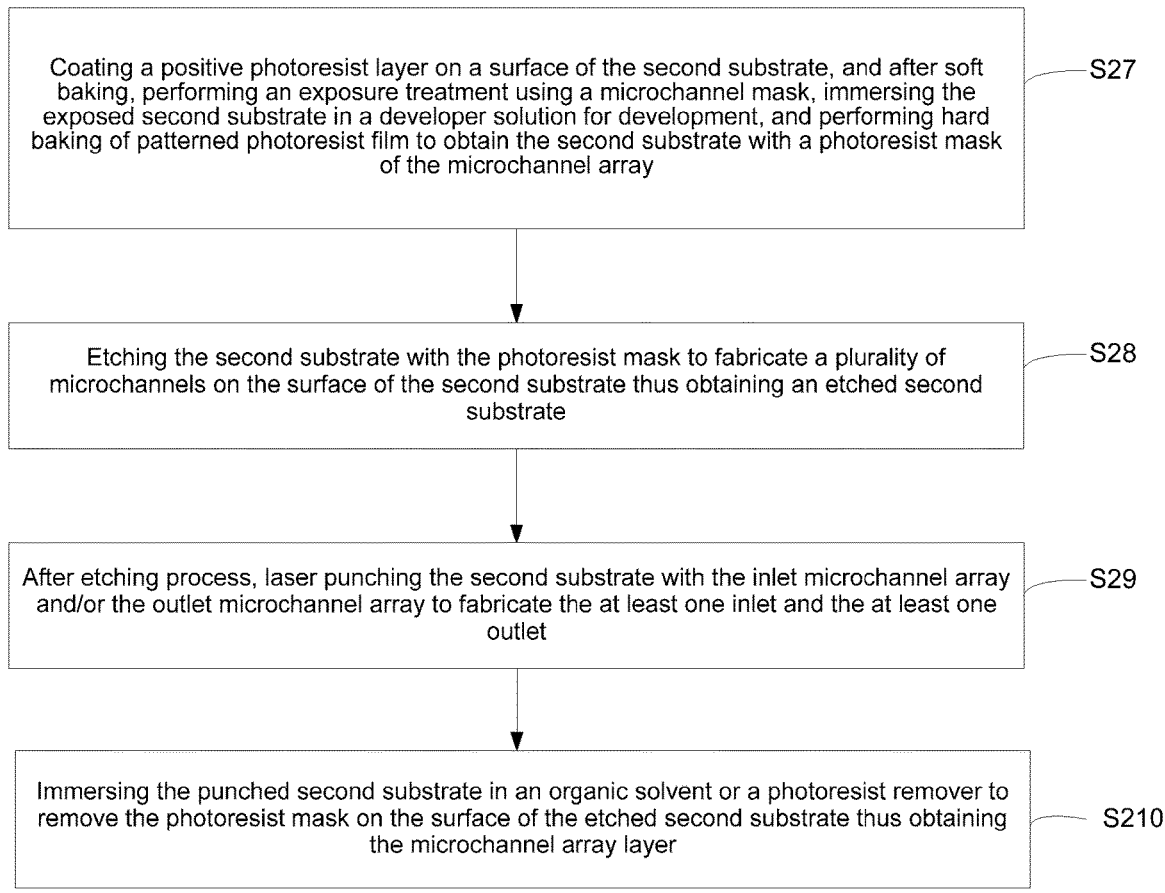
FIG. 13 is a flowchart of a method of fabricating the microchannel array layer according to another embodiment of this disclosure.

In particular, in another embodiment, as illustrated by FIG. 13, in S20, the input unit and the output unit are fabricated on the second substrate, where the input unit includes an inlet microchannel array and at least one inlet, and the output unit includes an outlet microchannel array and at least one outlet, and the operation of fabricating the microchannel array layer may be as follows.

In S27, a positive photoresist layer is coated on the surface of the second substrate. After soft baking, an exposure treatment is performed using a microchannel mask. Then the exposed second substrate is immersed in a developer solution for development, and the patterned photoresist film on the developed second substrate is hard baked to obtain the second substrate with a photoresist mask of the microchannel array.

In S28, the second substrate with the photoresist mask is etched to fabricate a plurality of microchannels on the surface of the second substrate thus forming the etched second substrate.

In S29, after the microchannels are fabricated by the etching process, the second substrate with the inlet microchannel array and/or the outlet microchannel array is laser-punched to obtain the at least one inlet and the at least one outlet.

In S210, the punched second substrate is immersed in an organic solvent or a photoresist remover, so that the photoresist mask on the surface of the etched second substrate is removed to obtain the microchannel array layer.

In particular, in one embodiment, in S30, the operation of alternately stacking and bonding the at least one nanochannel array layer and the at least one microchannel array layer includes subjecting the top surface of the first substrate and the bottom surface of the second substrate to oxygen plasma treatment, and then aligning and bonding the top surface of the first substrate with the bottom surface of the second substrate, as illustrated by i in FIG. 12.

In one embodiment, the method for fabricating the micro- and nano-fluidic chip further includes the following operations: connecting catheters to the inlet and the outlet of the second substrate; see j in FIG. 12, where the inlet catheter is used for sample input, and the outlet catheter is used for sample output.

The above-described micro- and nano-fluidic chip can be used for on-chip experiments of preparing cargo-carrying biological particles such as EVs. Therefore, the method of use and operation steps of the micro- and nano-fluidic chip on the cargo loading of EVs will be described in further detail below. On-chip experiments mainly include isolation of EVs, cargo mixing, chip treatment, cargo diffusion, and sample collection.

Figure 14:
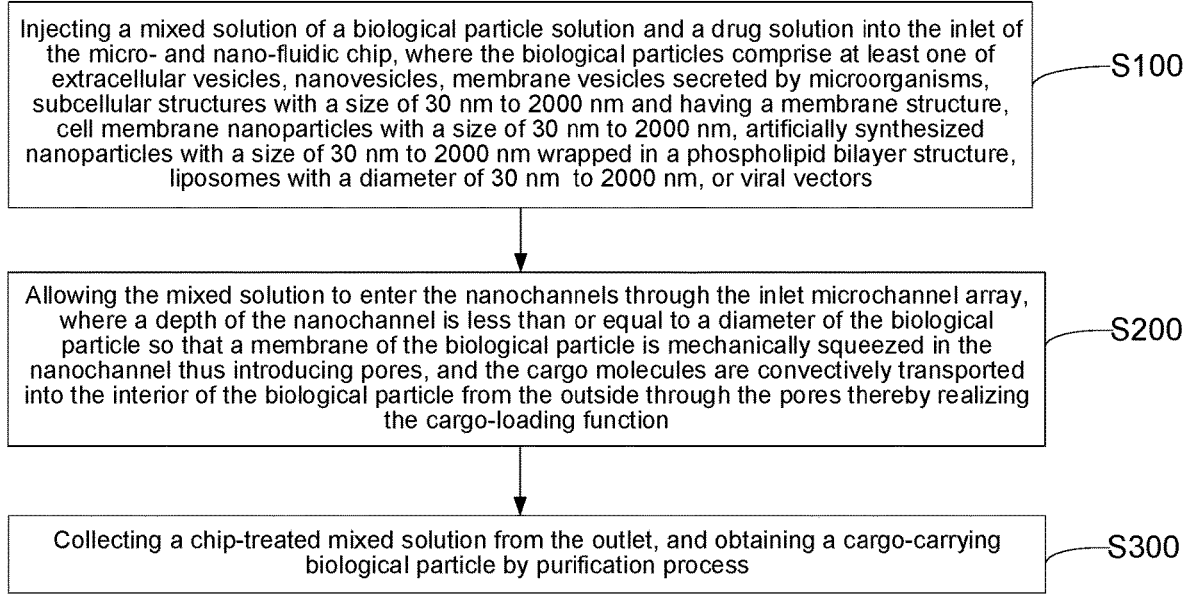
FIG. 14 is a flowchart of a method of preparing cargo-carrying biological particles according to an embodiment of this disclosure.

Now referring to FIGS. 14 and 15, there is provided a method for preparing cargo-carrying biological particles, the method including the following operations.

In S100, the method includes injecting a mixed solution of a biological particle solution of and a cargo solution into the inlet of the above-described micro- and nano-fluidic chip, where the biological particles include at least one of EVs, nanovesicles, membrane vesicles secreted by the microorganisms, subcellular particles with a size of 30 nm to 2000 nm and having a membrane structure, cell membrane nanoparticles with a size of 30 nm to 2000 nm, artificially synthesized nanoparticles with a size of 30 nm to 2000 nm wrapped in a phospholipid bilayer, liposomes with a diameter of 30 nm to 2000 nm, or viral vectors, etc.;

In S100, in the case where the biological particles are the EVs, the preparation of the biological particle solution includes the following operations:

In S110, the preparation includes isolating EVs from a biological sample.

In the operation of isolating EVs from a biological sample, one or a combination of several of the following commonly used methods for isolating EVs may be used: an ultracentrifugal isolation method, a density gradient centrifugal isolation method, a filtration isolation method, an immunocapture isolation method, a precipitation kit isolation method, a size-exclusion chromatography, a microfluidic-based isolation method, a polymer precipitation isolation method, and so on.

Further, the biological sample is cell culture supernatant, plasma, serum, urine, saliva, cerebrospinal fluid, ascitic fluid, amniotic fluid, semen, synovial fluid, bronchial fluid, tears, bile, gastric acid, lymph, pleural effusion, gastrointestinal lavage fluid, bronchoalveolar lavage fluid, milk, grape, grapefruit, lemon, watermelon, carrot, ginger, tomato, broccoli, or *ginseng*, etc.

In S120, the preparation includes resuspending the EVs in a PBS, cell culture medium, or normal saline, etc. to obtain the biological particle solution.

It will be appreciated that the exogenous cargos selected for biological particle loading will not be limited to a specific cargo. The cargo may be at least one of the drug cargos, protein cargos, nanomaterial cargos, nucleic acid cargos, or biomolecule cargos, etc. with a size of 500 nm or less.

Further, the drugs with a size less than or equal to 500 nm may be anticancer drugs, drugs for infectious disease, drugs for cardiovascular diseases, drugs for neurodegenerative diseases, or drugs for autoimmune diseases, etc.

Further, the anticancer drugs include doxorubicin, curcumin, and paclitaxel, etc.

The drugs for infectious disease include amphotericin B, ciprofloxacin, rifampicin, and tobramycin, etc.

The drugs for cardiovascular disease include amiodarone, atenolol, and isosorbide-5-mononitrate, etc.

The drugs for neurodegenerative disease include tanshinone IIA, levodopa, donepezil, and memantine, etc.

The drugs for autoimmune disease include tacrolimus and dexamethasone sodium phosphate, etc.

The protein cargos include immunoglobulin, interleukin, bovine serum albumin, endonuclease, and Cas9 protein, etc.

The nanomaterial cargos include quantum dots, carbon nanotubes, nanoparticles, etc.

The nucleic acid cargos include plasmids, ribonucleic acids, and oligonucleotides, etc.

The biomolecule cargos include potassium ion probe molecules, calcium ion probe molecules, and inositol triphosphate, etc.

In S100, in the mixed solution of the biological particle solution and the cargo solution, the concentration of the biological particle solution and the concentration of the cargo solution may be set according to actual requirements.

The mixed solution is injected into the inlet microchannel of the micro- and nano-fluidic chip through an inlet catheter. Due to the obstruction effect of the EV membrane, the cargo molecules can only be distributed outside the EVs, as illustrated by a in FIG. 15.

In S200, the mixed solution enters the nanochannel through the inlet micro channel. Since the depth of the nanochannel is less than or equal to the diameter of the biological particles, the membrane of the biological particles is mechanically squeezed in the nanochannel so as to introduce pores, and the cargo molecules are convectively transported into the interior of the biological particles from the outside through the pores thus realizing the cargo-loading function.

In particular, in the case where the biological particles are EVs, after the mixed solution is injected into the inlet microchannel, the EVs and the cargo molecules are squeezed by the nanochannels and then arrive at the outlet microchannel, where the depth of the nanochannels is less than or equal to the diameter of the EVs. Then the transient pores are introduced in the membrane of the EVs under the mechanical compression of the nanochannel thus providing a pass way for cargo transportation, see b in FIG. 15. Specifically, when the EVs enter the smaller nanochannels, the EVs are deformed under the mechanical compression. During this process, the mechanical compression will provide energy to the membrane of the EVs, resulting in reconstitution of the phospholipid bilayer, thereby introducing pores during the reconstitution process.

In the outlet microchannel, when pores are introduced in the surface of the EV membrane, the cargo molecules are convectively transported from the outside of the EVs into the inside through these pores under the mechanical effects. Then the EV membrane gradually restores to its intact form, thereby realizing the cargo-loading function, as illustrated by c in FIG. 15. In particular, after the EV membrane is permeabilized, the calcium ion concentration inside and outside the EVs will change, thereby driving the EVs to repair their membranes.

In S300, the chip-treated mixed solution is collected from the outlet, and the cargo-carrying biological particles are obtained by purification process.

That is, in S300, the purification method may include ultracentrifugation, density gradient centrifugation, filtration, immunocapture, precipitation kit method, size-exclusion chromatography, microfluidic-based method, and polymer precipitation, etc.

In the above-described method for preparing cargo-carrying biological particles, the biological particles will not be limited to being mixed with a special cargo, and may also be mixed with multiple cargos at the same time, so that the multiple cargos can be loaded into the biological particles simultaneously. In addition, in the case where the biological particles are EVs, the size of the EVs is about 30 nm~2000 nm. The EVs involved in cargo loading however will not be limited to a specific size, and the EVs that come in multiple sizes may be squeezed for cargo loading in the same micro- and nano-fluidic chip.

After the cargo-carrying biological particles are prepared, their structure and function are also characterized. In particular, after the cargo-carrying biological particles are obtained, the cargo-loading efficiency, the morphology, and the electrokinetic potential of these biological particles can be characterized using one or more selected from the following analytical methods, including flow cytometry, superresolution optical imaging system, scanning electron microscope, transmission electron microscope, atomic force microscope, cryo-electron microscope, nanoparticle tracking analysis, and so on. In addition, functional characterization of the cargo-carrying biological particles may also be performed, for example, co-incubating the cargo-carrying biological particles with different types of cells or tissues in vitro, and observing the process of the biological particles delivering cargos into these cells or tissues in vitro. Additionally or alternatively, the cargo-carrying biological particles may also be used to carry out animal experiments to explore the treatment process and therapeutic effect of biological particles carrying cargos to the lesion or focal tissue in the animal body.

In addition, referring to FIG. 16, there is further provided another method for preparing cargo-carrying biological particles, the method including the following operations.

In S400, a solution of biological particles is injected into the inlet of the above-described micro- and nano-fluidic chip, where the biological particles include at least one of EVs, nanovesicles, membrane vesicles secreted by the microorganisms, subcellular particles with a size of 30 nm to 2000 nm and having a membrane structure, cell membrane nanoparticles with a size of 30 nm to 2000 nm, artificially synthesized nanoparticles with a size of 30 nm to 2000 nm wrapped in a phospholipid bilayer, or liposomes with a diameter of 30 nm to 2000 nm, viral vectors, etc.

In S500, the solution of biological particles enters the nanochannels through the inlet microchannels. Since the depth of the nanochannel is less than or equal to the diameter of the biological particles, the membrane of the biological particles is mechanically squeezed in the nanochannel so as to introduce pores.

In S600, the solution of the biological particles having been squeezed is collected from the outlet, and mixing the exogenous cargos with the squeezed biological particle solution, so that the cargo molecules diffuse into the interior of the biological particles from the outside through the pores, and further obtaining the cargo-carrying biological particles by purification process.

In addition, the above-described micro- and nano-fluidic chip can not only be used for squeezing biological particles for cargo loading, but also for applications in synthesizing liposomes and squeezing the liposomes for cargo loading, synthesizing cell membrane fragments into cell membrane nanoparticles and squeezing them for cargo loading, or the application in cargo loading of artificially synthesized nanoparticles that are wrapped by a phospholipid bilayer.

The above-described micro- and nano-fluidic chip has a unique layout. In particular, by way of connecting the nanochannel array to the microchannel array, the demand for cargo loading of biological particles such as EVs can be achieved, and different experimental throughputs can also be achieved. The design of the micro- and nano-fluidic chip is scalable, that is, the number and shape of the microchannel array and nanochannel array can be designed according to experimental requirements. The method of fabricating the micro- and nano-fluidic chip is simple and diverse and easy to implement. The layout parameters of the nanochannel array have the characteristics of high throughput and flexible design. For example, the depth, width, length, spacing, and number can be designed or changed according to requirements of cargo-loading throughput, sizes of exogenous cargos, or requirements of cargo-loading efficiency. The cargo loading of biological particles such as EVs is versatile for all types and sizes of exogenous cargos. In particular, one or more drug cargos, protein cargos, nanomaterial cargos, nucleic acid cargos, or biomolecule cargos may be loaded at the same time into different types or sizes of EVs (30 nm~2000 nm in size), nanovesicles (30 nm~2000 nm in size), subcellular particles having membrane structures (30 nm~2000 nm in size), cell membrane nanoparticles (30 nm~2000 nm in size), artificially synthesized nanoparticles (30 nm~2000 nm in size) wrapped by a phosphate bilayer, liposomes (30 nm~2000 nm in size), or membrane vesicles (30 nm~2000 nm in size) secreted by bacteria and other microorganisms. Biological particles such as EVs are versatile for all types of drug cargos, protein cargos, nanomaterial cargo, nucleic acid cargos, or biomolecule cargos, as long as it is satisfied that the size is less than or equal to 500 nm.

As used herein, directional or direction of extensional terms such as "up", "down", "front", "rear", "left", and "right", etc., merely indicate reference directions or direction of extensions and are not used to limit the present disclosure. The specific embodiments described above further describe the objectives, technical solutions, and beneficial effects of the present disclosure in detail. It should be understood that the foregoing description are merely some specific embodiments according to the present disclosure but are not intended to limit the present disclosure. For those having ordinary skill in the art, any modification, equivalent substitution, improvement, etc. made within the spirit and principle of the present disclosure should all fall in the scope of protection of the present disclosure.

What is claimed is:

1. A micro- and nano-fluidic chip, comprising at least one nanochannel array layer and at least one microchannel array layer, the at least one nanochannel array layer and the at least one microchannel array layer being alternately stacked;
   wherein the at least one nanochannel array layer comprises multiple nanochannels;
   wherein the at least one microchannel array layer comprises an input unit and an output unit; the input unit comprises at least one inlet microchannel and at least one inlet, and the output unit comprises at least one outlet microchannel and at least one outlet; wherein the at least one inlet microchannel and the at least one outlet microchannel are alternately arranged at intervals; the at least one inlet is connected to the at least one inlet microchannel, and the at least one outlet is connected to the at least one outlet microchannel; each pair of inlet microchannel and outlet microchannel are bridged by the at least one nanochannel;
   wherein the number of the at least one microchannel array layer is one, the microchannel array layer comprises the input unit and the output unit, the nanochannel array layer connects the at least one inlet microchannel and the at least one outlet microchannel, and the extension direction of the nanochannels is set at an angle of 0°~90° with the microchannel array layer.

2. The micro- and nano-fluidic chip of claim 1, wherein the at least one nanochannel array layer is made of polydimethylsiloxane (PDMS), glass, quartz, silicon wafer, silicon nitride wafer, silicon dioxide wafer, silicon carbide wafer, poly (methyl methacrylate) (PMMA), parylene-C, polycarbonate (PC), cyclic olefin copolymer (COC), cyclic olefin polymer (COP), polypropylene (PP), photocurable resin, or soft thermoplastic elastomer (sTPE), and the at least one microchannel array layer is made of PDMS, glass, quartz, silicon wafer, silicon nitride wafer, silicon dioxide wafer, silicon carbide wafer, PMMA, or parylene-C, PC, COC, COP, PP, photocurable resin, or sTPE.

3. The micro- and nano-fluidic chip of claim 1, wherein the nanochannels of the at least one nanochannel array layer are arranged at an angle of 0° to 90° with respect to each other.

4. The micro- and nano-fluidic chip of claim 1, wherein there are provided one inlet microchannel and one outlet microchannel, the inlet microchannel and the outlet microchannel are arranged at an angle of 0° to 90° with respect to each other; or
 there are provided two or more inlet microchannels and two or more outlet microchannels, the inlet microchannels are arranged in parallel, the outlet microchannels are arranged in parallel, and the inlet microchannels are arranged in parallel with the outlet microchannels forming a parallel interdigitated layout; or
 there are provided two or more inlet microchannels and two or more outlet microchannels, the inlet microchannels are arranged at an angle of greater than 0° and less than or equal to 90° with respect to each other, the outlet microchannels are arranged at an angle of greater than 0° and less than or equal to 90° with respect to each other, and the inlet microchannels and the outlet microchannels are arranged to form an oblique interdigitated layout; or
 the at least one inlet microchannel has a circular shape, the at least one outlet microchannel has an annular shape, and the at least one inlet microchannel and the at least one outlet microchannel form a circular interdigitated layout; or
 the at least one inlet microchannel has an annular shape, the at least one outlet microchannel has a circular shape, and the at least one inlet microchannel and the at least one outlet microchannel form a circular interdigitated layout; or
 the at least one inlet microchannel has a spiral shape, the at least one microchannel has a spiral shape, and the at least one inlet microchannel and the at least one outlet microchannel form a spiral interdigitated layout.

5. The micro- and nano-fluidic chip of claim 1, wherein the at least one inlet microchannel has a depth of 1 μm to 1000 μm, and the at least one outlet microchannel has a depth of 1 μm to 1000 μm;
 the at least one nanochannel has a rectangular parallelepiped shape, the at least one nanochannel has a depth dimension of 10 nm to 5000 nm, and a width dimension of 10 nm to 1000 μm; or
 the at least one nanochannel has a cylindrical shape, the at least one nanochannel has a diameter of 10 nm to 5000 nm.

6. A micro- and nano-fluidic chip, comprising at least one nanochannel array layer and at least one microchannel array layer, the at least one nanochannel array layer and the at least one microchannel array layer being alternately stacked;
 wherein the at least one nanochannel array layer comprises multiple nanochannels;
 wherein the at least one microchannel array layer comprises an input unit and an output unit; the input unit comprises at least one inlet microchannel and at least one inlet, and the output unit comprises at least one outlet microchannel and at least one outlet; wherein the at least one inlet microchannel and the at least one outlet microchannel are alternately arranged at intervals; the at least one inlet is connected to the at least one inlet microchannel, and the at least one outlet is connected to the at least one outlet microchannel; each pair of inlet microchannel and outlet microchannel are bridged by the at least one nanochannel;
 wherein the number of the at least one microchannel array layer is two or more, one of the microchannel array layers comprises the input unit, and another of the microchannel array layers comprises the output unit, and the nanochannel array layer is arranged between every two adjacent microchannel array layers; the nanochannel array layer connects the at least one inlet microchannel and the at least one outlet microchannel, and an extension direction of the nanochannels is set at an angle of 0°~90° with the microchannel array layers.

* * * * *